(12) United States Patent
King et al.

(10) Patent No.: US 6,722,530 B1
(45) Date of Patent: *Apr. 20, 2004

(54) SYSTEM FOR DISPENSING CONTROLLED AMOUNTS OF FLOWABLE MATERIAL FROM A FLEXIBLE CONTAINER

(75) Inventors: Kenyon M. King, Rancho Cucamonga, CA (US); Gregory D. King, Alta Loma, CA (US)

(73) Assignee: Restaurant Automation Development, Inc., Rancho Cucamonga, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/690,355

(22) Filed: Oct. 16, 2000

Related U.S. Application Data

(63) Continuation-in-part of application No. 08/909,783, filed on Aug. 11, 1997, now Pat. No. 6,131,766.
(60) Provisional application No. 60/135,508, filed on Aug. 12, 1996.

(51) Int. Cl.$^7$ .................................................. B67D 5/00
(52) U.S. Cl. .................... 222/82; 222/83.5; 222/96; 222/105; 222/146.2; 222/326; 222/390
(58) Field of Search ........................... 222/81, 82, 83, 222/83.5, 88, 96, 105, 146.2, 326, 333, 390

(56) References Cited

U.S. PATENT DOCUMENTS

| | | | |
|---|---|---|---|
| 3,242,881 A | 3/1966 | Schafer | 222/390 |
| 3,904,083 A | 9/1975 | Little | 222/82 |
| 3,926,339 A | 12/1975 | Openchowski | 222/83 |
| 4,098,434 A | 7/1978 | Uhlig | 222/94 |
| 4,138,036 A | 2/1979 | Bond | 222/105 |
| 4,335,834 A | 6/1982 | Zepkin | 222/63 |
| 4,356,938 A | 11/1982 | Kayser | 222/327 |
| 4,572,409 A | 2/1986 | Finnegan | 222/391 |
| 4,635,820 A | 1/1987 | Marshall | 222/63 |
| 4,865,224 A | 9/1989 | Streck | 222/95 |
| 4,869,405 A | 9/1989 | Rudick | 222/518 |
| 4,884,705 A | 12/1989 | Debetencourt | 215/250 |
| 5,002,202 A | 3/1991 | Karpisek | 222/83 |

(List continued on next page.)

FOREIGN PATENT DOCUMENTS

| | | |
|---|---|---|
| DE | 40 31 777 A1 | 5/1991 |
| DE | 92 17 062 | 4/1993 |
| DE | 43 28 735 A1 | 3/1995 |
| EP | 0 002 987 A1 | 12/1978 |
| JP | 5-34184 | 2/1993 |

OTHER PUBLICATIONS

"Economy Cordless Caulk Gun," *McMaster–Carr catalog*, p. 2962.

*Primary Examiner*—Joseph A. Kaufman
(74) *Attorney, Agent, or Firm*—Knobbe, Martens, Olson & Bear, LLP

(57) ABSTRACT

A system for dispensing controlled amounts of flowable materials having a wide range of viscosities, such as food condiments, caulking or adhesives, from a flexible-walled container or bag includes a housing for holding the flexible-walled container and a piston positioned within the housing to apply pressure to a wall of the flexible-walled container. An enfitment, which has a piercing member and sealing mechanism, is positioned adjacent an opposite wall of the flexible-walled container. By rotating the enfitment about a rotational axis generally normal to the wall of the first container, the enfitment forms an opening in the flexible-walled container and a seal with the container. The flowable material can then be forced through a hollow tube of the enfitment and an exit nozzle coupled to the enfitment. A desired amount of flowable material can be consistently dispensed from the flexible-walled container by controlling the displacement of the piston along a predetermined piston travel length for each dispensation of flowable material.

20 Claims, 17 Drawing Sheets

U.S. PATENT DOCUMENTS

| | | |
|---|---|---|
| 5,105,997 A | 4/1992 | Wakabayashi et al. ...... 222/494 |
| 5,123,570 A | 6/1992 | Dubow ........................ 222/83 |
| 5,127,550 A | 7/1992 | Knorr ......................... 222/83 |
| 5,156,300 A | 10/1992 | Spahni et al. ............... 222/105 |
| 5,219,099 A | 6/1993 | Spence et al. .............. 222/325 |
| 5,236,105 A | 8/1993 | Galex ........................... 222/1 |
| 5,273,186 A | 12/1993 | Widmer ....................... 222/50 |
| 5,288,021 A | 2/1994 | Sood et al. .............. 239/132.5 |
| 5,348,585 A | 9/1994 | Weston ....................... 118/305 |
| 5,351,889 A | 10/1994 | Whiteside |
| 5,429,273 A | 7/1995 | King et al. .................... 222/82 |
| 5,435,462 A | 7/1995 | Fujii ........................... 222/82 |
| 5,505,336 A | 4/1996 | Montgomery et al. ........ 222/82 |
| 5,553,740 A | 9/1996 | King et al. ..................... 222/1 |
| 5,556,009 A | 9/1996 | Motzko ...................... 222/326 |
| 5,775,533 A | 7/1998 | Schroeder .................... 222/95 |
| 6,131,766 A | * 10/2000 | King et al. ..................... 222/1 |

* cited by examiner

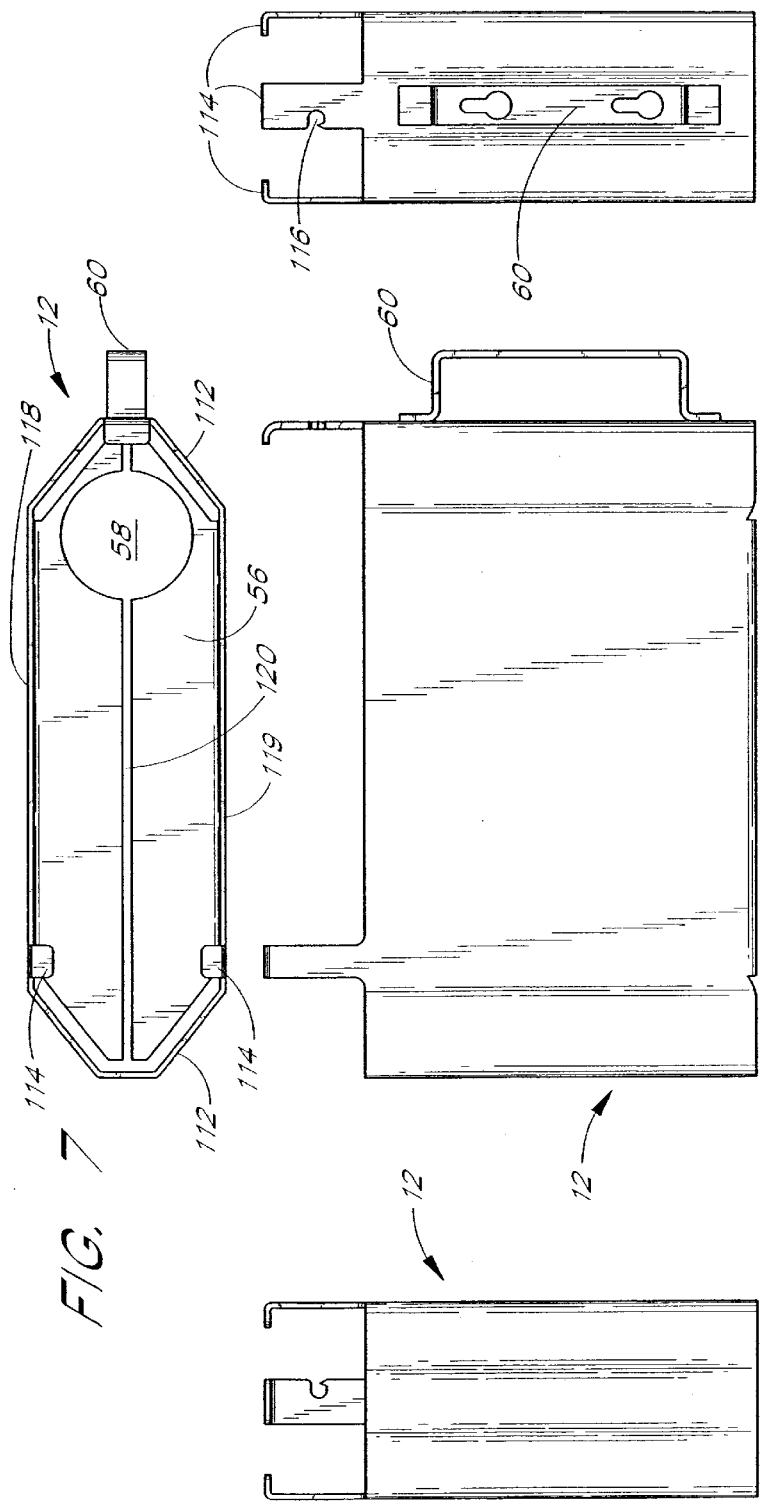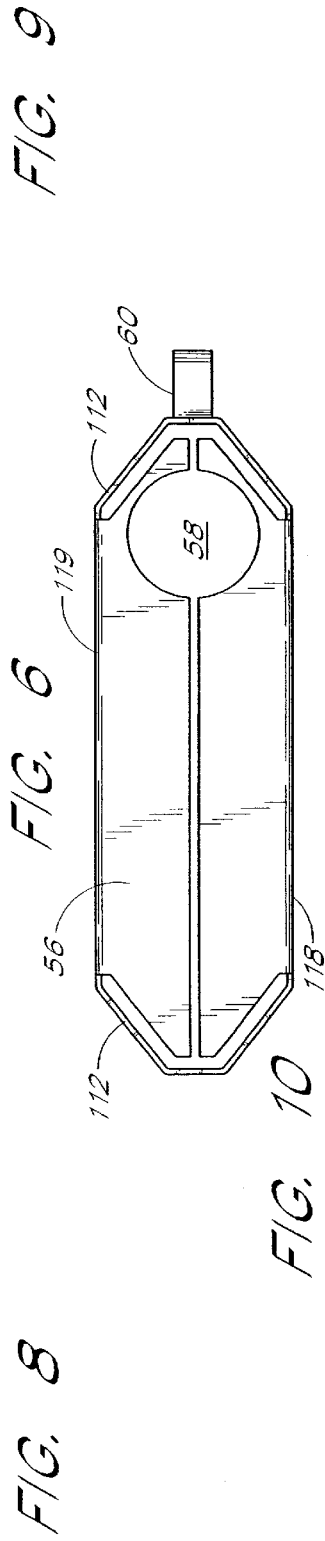

*0 DEGREE ROTATION*

*90 DEGREE ROTATION*

*180 DEGREE ROTATION*

*270 DEGREE ROTATION*

*360 DEGREE ROTATION*

*450 DEGREE ROTATION*

SYSTEM FOR DISPENSING CONTROLLED AMOUNTS OF FLOWABLE MATERIAL FROM A FLEXIBLE CONTAINER

RELATED CASE

This application is a continuation-in-part of U.S. application Ser. No. 08/909,783, filed Aug. 11, 1997, now U.S. Pat. No. 6,131,766, which claims the benefit of priority under 35 U.S.C. §119(e) of U.S. application Ser. No. 08/689,439, originally filed as a non-provisional application on Aug. 12, 1996, which has been converted to provisional U.S. Application Ser. No. 60/135,508.

FIELD OF THE INVENTION

The present invention relates in general to an improved system for dispensing controlled amounts of flowable material from within sealed flexible-walled containers, and in particular, to devices which press-pump materials having wide ranges of viscosities, temperatures, and particulate contents from flexible-walled containers.

BACKGROUND OF THE INVENTION

The restaurant and consumer products industries are making increased use of flexible bags to contain food products. These bags are easy to handle and require less storage and shipping space. The flexible bags can be easily loaded into dispensers for dispensation of the food product, thereby reducing handling of the food product.

Flexible-walled bottles have long been used to dispense fluids by squeezing. Such bottles have been usually made with resilient walls which tend to restore to their original shape after removal of deforming forces. As the ratio of inside air to liquid increases with bottle use, difficulties are encountered in attempting to completely empty the bottle in a timely manner. Solutions to these problems have included placement of the fluid in an inner bag which is sealed within a squeeze bottle. Examples of such structures have been disclosed by Streck in U.S. Pat. No. 4,865,224 and Uhlig in U.S. Pat. No. 4,098,434.

Although the above solutions decreased the time required to empty the squeeze bottle, new problems associated with premature bag collapse and with potential exit orifice blockage arose. Semi-rigid internal bag cartridges which lessen these problems and various supporting structures placed inside the bag are known, such as the apparatus disclosed in U.S. Pat. No. 5,156,300 issued to Spahni et al. Combinations of such internal bag elements with dispensing means are also available. For example, in U.S. Pat. No. 4,138,036 to Bond a helical coil bag insert is coupled with a dispensing spout supported in the neck opening of a rigid external structure.

In addition, other combination devices have mated a protected dispensing orifice with a bag cutting and sealing means. An example of this approach is shown by Knorr in U.S. Pat. No. 5,127,550, wherein a first member having a throughbore therein is used in conjunction with a cutting means to seal adjacent portions of a bag wall together while piercing the bag wall for fluid release through the narrow passages cut therein.

Some prior art enfitments which are designed to penetrate a flexible bag protrude into the bag. The protruding portion of the enfitment interferes with piston or bag compression types of pumping. Also, the protruding device traps product that cannot be dispensed, thus, increasing waste of undispensed flowable material. These problems are increased when the food products include varied viscosity items, such as condiments, and when it is desirable to perform such tasks automatically.

The protruding enfitment device also interferes with a piston or bag compression type of pump for pumping the material from the bag. Further, such enfitment devices are often difficult to attach to the bag. These problems become worse when the bag contains material, such as food products, of various viscosity, such as condiments, and when it is desirable to perform such tasks automatically. In the restaurant industry, for instance, existing devices have been mostly useful in manual dispensing of condiments by customers.

In the area of rapid food preparation, especially in quick-service restaurants, a need exists to dispense controlled portions of a broad spectrum of material having uneven flow characteristics. Such materials include food products with variable viscosities, emulsions, colloidal suspensions which can coagulate or settle out with time, as well as semi-solid mixtures, such as relish, beans, meat, sour cream, cheese sauces, ketchup, or mustard. These materials must be moved or pumped in a manner in which the flowable material or product maintains its piece integrity. As an example, emulsions or suspensions must not be overworked to cause a shearing action or breaking of the emulsion.

Further difficulties arise in obtaining repeatable dispensations of a controlled amount of flowable material, especially when the temperature and viscosity of the flowable material varies over a wide range. The portion or amount of ingredient that is pumped from a flexible-walled container is usually dependent on one or more of the following: the amount of pressure, duration of pressure application, pressure-sensitive valves, exit hole size and product viscosity. For instance, if the time that the pressure is applied to the container is held constant, then the ingredient portion being dispensed will become smaller as the residual ingredient left in the bag is reduced.

Current dispensation of food products from flexible bags is achieved by transferring the food product into mechanical handheld dispensing devices or through the use of enfitments. Enfitments are attached to the bag and used to interface with a dispense hose or nozzle. Such enfitments can be either placed on the bag before loading within the device or attached within the handheld device. Each method, however, requires either additional labor to attach the enfitment to the bag or takes up space within the mechanical handheld device. In addition, manual attachment of the enfitment to the bag increases handling of the food ingredients and creates undesirable food handling risks.

SUMMARY OF THE INVENTION

The present invention provides a system for dispensing controlled amounts of flowable material which is stored in a flexible-walled container. The system of the present invention includes a second container configured to hold a first flexible-walled container, a piston, and an actuator connected to the piston to drive the piston along a stroke axis through a preset travel range. The system can be constructed in a modular manner to allow multiple dispensing systems to be placed in a space efficient manner in-line with varying sizes of storage capacities.

A flexible bag or other flexible-walled container containing flowable food product is positionable within the second container. The cross-sectional shape of the second container, as taken generally normal to the stroke axis of the system, is complementary to the cross-sectional shape of the first container.

The present invention further provides an enfitment which can be automatically or manually attached to the flexible-walled container or bag for dispensing flowable material contained within the bag. The enfitment, which extends through a wall of the second container, includes a piercing member to puncture the wall of the first container to form an opening and a sealing mechanism to seal the opening of the first container around the enfitment. The enfitment further includes a hollow tube having inner and outer surfaces and first and second open ends with the piercing member being formed at one end of the hollow tube. The piercing member and sealing mechanism are configured to interact with the wall of the flexible-walled container to form an opening in the container through which the flowable material can pass through the hollow tube and to stretch the opening around the outer surface of the hollow tube. The piercing member has a sharpened tip to penetrate the wall of the flexible-walled container.

The piston is positionable within the second container above the first container to apply pressure to at least a wall of the first flexible-walled container so as to compress the first flexible-walled container between the piston and the enfitment. The enfitment extends through a wall of the second container opposite the wall of the first flexible-walled container adjacent to the piston. In an automated embodiment, a drive mechanism rotates the enfitment about a rotational axis generally normal to a wall of the second container. As the enfitment is rotated, the piercing member punctures the flexible wall of the first container and the sealing mechanism interacts with the first container to form a seal therewith.

The enfitment is shaped so that the bag can be easily removed from the enfitment. As the enfitment is rotated in a reverse direction, a recess in the sealing mechanism guides the bag opening upward relative to the enfitment to unseal the flexible container from the enfitment. In an automated embodiment, the drive mechanism is simply reversed to unwind the enfitment from the flexible bag. Thus, the enfitment can be automatically attached to and detached from the bag by rotating the enfitment in an opposite rotational directions.

In a preferred embodiment, a piston includes a recess shaped to receive the portion of the enfitment which protrudes into the first container. For instance, a circular-shaped recess in a piston can receive a generally circular-shaped piercing member and sealing mechanism of the enfitment. Thus, as the piston reaches the end of its overall predetermined stroke length, a portion of the enfitment is received within the recess portion of the piston. In this manner, the amount of material dispensed from the bag can be maximized.

For dispensation of a controlled amount of flowable material from the flexible-walled container, the piston is actuated through a series of sequential dispensation steps. During each dispensation step, the piston is moved by a predetermined stroke length toward the first container to dispense a desired amount of material from the first container. A controlled displacement motor can be used to move the piston through the series of sequential dispensation steps.

Because the flexible-walled container can have an uneven shape, the predetermined stroke length of the piston for each dispensation step within the series of sequential dispensation steps can differ between at least two of the dispensation steps to achieve controlled dispensation of a predetermined amount of flowable material. As the bag sits within the second container or ingredient hopper, the top surface of the bag does not necessarily mirror the shape of the hopper. Toward the middle and bottom of the bag, the cross-sectional shape of the bag tends to be the same as the cross-sectional shape of the second container. Thus, if the piston travel for each dispensation step is constant, the amount of food product dispensed on the first few dispensations will be smaller than the amount of product later dispensed as the shape of the bag fills the entire shape of the second container.

The present invention provides a method for dispensing a controlled amount of flowable material from the flexible-walled container which includes determining the quantity of flowable material in the flexible-walled container, ascertaining the amount of piston travel for compressing the flexible-walled container within the second container which is required to dispense a desired amount of material from the flexible-walled container based on the determined quantity of flowable material in the flexible-walled container, and controlling the displacement of the piston to move the piston by the ascertained distance to dispense a predetermined amount of the material.

During the first dispensation step of the series of sequential dispensation steps, the piston can be moved by a stroke which is longer than the stroke length associated with a median dispensation step of the series of sequential dispensation steps. In this manner, generally the same amount of material which is dispensed at the first dispensation is also dispensed at the median dispensation.

Depending on the type of material to be dispensed, piston velocity can be also controlled in order to control product flow rate. In addition, in a preferred embodiment of the present invention, after dispensation associated with each sequential dispensation step of moving the piston toward the first container, the piston is moved by reverse travel away from the first container to reduce the pressure of the flowable material within the first container. Since continuing pressure on the first container can cause undesirable dripping of the flowable material, this back-up feature reduces dripping from an exit nozzle coupled to the first container through which the flowable material is dispensed. A pressure-release valve disposed within the exit nozzle can be used to control flow of the material from the first container so that material is dispensed as pressure is applied to the first container by the piston, yet when the pressure is reduced dripping from the nozzle is reduced or eliminated.

A method for dispensing controlled amounts of flowable material stored in a first flexible-walled container involves providing a base, positioning the first flexible-walled container in a second container being supported by the base, mounting a hollow enfitment through at least one wall of the second container for opening the first flexible-walled container and dispensing the flowable material therethrough, rotating a piston positionable within the second container to apply force to at least one wall of the first flexible-walled container so as to compress the first flexible-walled container between the piston and the enfitment, and driving the piston toward the base along a stroke axis to compress the first flexible-walled container against the second container to dispense the flowable material through the enfitment.

BRIEF DESCRIPTION OF THE DRAWINGS

The above-mentioned and other features of the invention will now be described with reference to the drawings of a preferred embodiment of the present invention. The illustrated embodiments are intended to illustrate, but not to limit the invention. The drawings contain the following figures:

FIG. 6 is a side elevational view of a hopper of the system illustrated in FIG. 1A, configured in accordance with a preferred embodiment of the present invention.

FIG. 7 is a top plan view of the hopper of FIG. 6.

FIG. 8 is a rear elevational view of the hopper of FIG. 6.

FIG. 9 is a front view of the hopper of FIG. 6.

FIG. 10 is a bottom plan view of the hopper of FIG. 6.

DETAILED DESCRIPTION OF THE PREFERRED EMBODIMENT

Figure 1A:
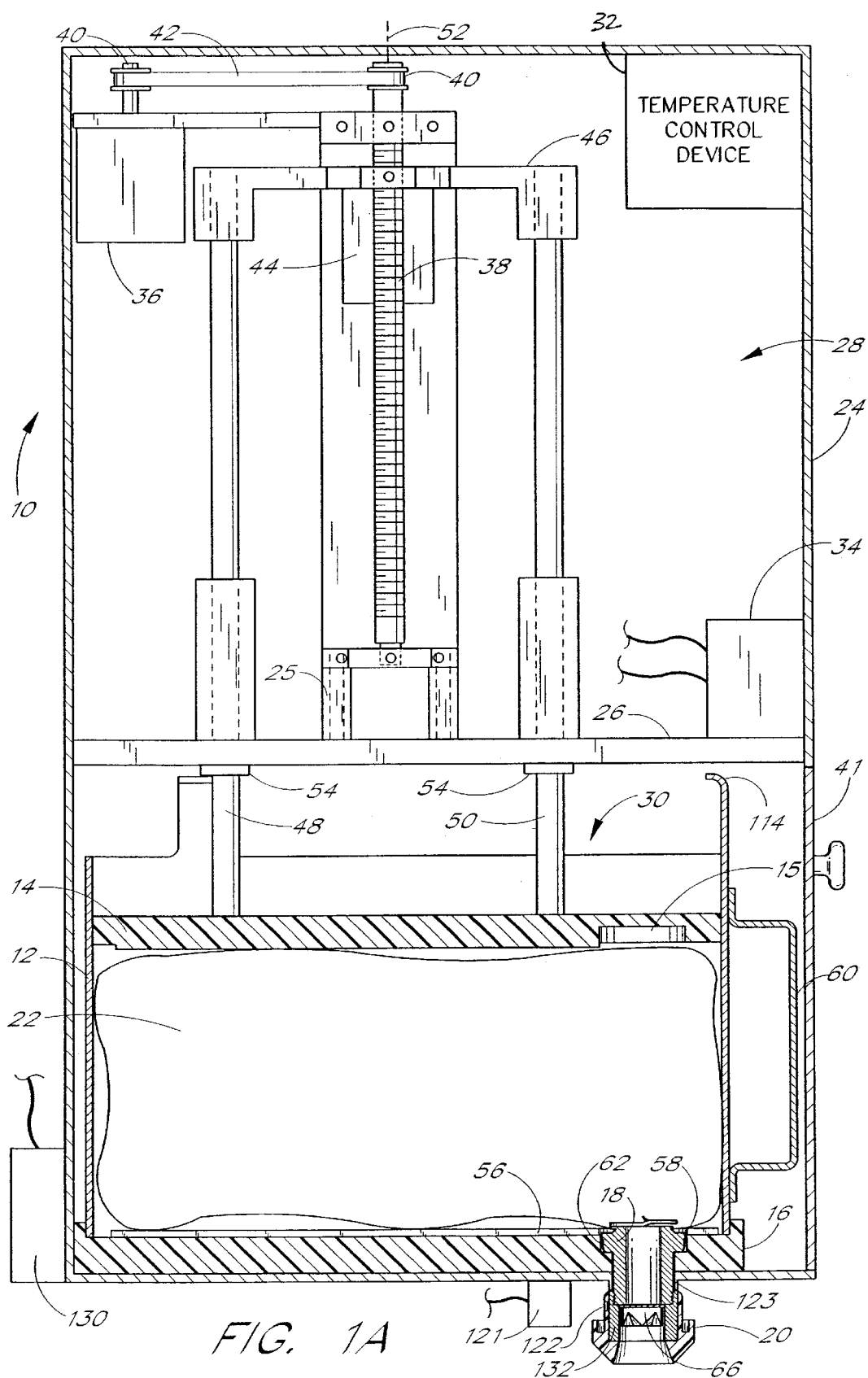
FIG. 1A is a side cross-sectional view of a system for pumping controlled amounts of flowable material from a flexible bag in accordance with the present invention.

FIG. 1A illustrates a side cross-sectional view of a system in accordance with the present invention for pumping controlled amounts of flowable material from a flexible-walled container. The flexible-walled container can include any container that has at least one wall which is flexible in shape and/or position relative to one or more of the other walls. Such containers include, but are not limited to, a bag, a tube, or a box with one or more collapsible and or movable side walls. As shown in FIG. 1A, the system 10 includes a rigid walled container or hopper 12, a piston 14 within the hopper, a base 16 which supports the hopper, an enfitment apparatus 18 and an exit nozzle assembly 20. A flexible-walled container, such as a bag 22, containing a flowable material to be dispensed, is placed within the hopper 12 beneath the piston 14. In the illustrated embodiment, the piston 14 applies pressure to the bag 22 on a side of the bag 22 opposite the side on which the enfitment engages the bag 22, and the enfitment 18 lies generally normal to a surface of the bag 22; however, those skilled in the art can readily adapt the orientations of these components to suit other applications, i.e., the enfitment 18 and a stroke axis 52 of the piston 14 may be disposed generally normal to each other.

In the illustrated embodiment, a cabinet 24 houses the base 16, hopper 12 and piston 14. In other applications, the hopper 12 can be connected to or unitary with the cabinet 24. A bulkhead 26 desirably divides the cabinet 24 into two compartments: drive mechanism compartment 28 and a pump compartment 30. A door 41 on a side (e.g., a front side) of the cabinet 24 provides easy access into at least the pump compartment 30. In this manner, a worker can insert a hopper 12, which contains an unopened, flexible-walled container 22, into the cabinet 24 and can remove the hopper 12 from the cabinet 24 once the content of the flexible-walled container 22 is spent. In other application, the door 41 can be unitary with the hopper 12 so that upon opening of the door 41, the hopper is also removed.

In the illustrated embodiment, a conventional temperature control system 32 maintains at least the pump compartment 30 at a desired temperature, either heated or cooled relative to an ambient temperature. The cabinet 24 can also be insulated (although this is not illustrated). In other applications, however, the temperature of the cabinet 24 need not be controlled.

The system of FIG. 1A further includes a motor 36 which drives a ball screw device having a lead screw 38 by way of a pair of pulleys 40 coupled by a belt 42. One of the pulleys 40 is fixed to the lead screw 38 and the other pulley 40 is fixedly coupled to a shaft of the motor 36. The lead screw 38 drives an assembly, which comprises a ball nut 44, a plate 46, transfer shafts 48, 50 and piston 14, linearly along a stroke or travel axis 52 of the lead screw 38. Those of ordinary skill in the art will recognize that movement of the piston can be accomplished by other drive mechanisms, such as, but not limited to, a rack and pinion device, jack screw device, and worm gear device. In addition, the drive mechanism can be configured such that the shaft moves with the piston, rather than the nut or gear. That is, the motor can drive the nut or gear which in turn causes the shaft to move along the stroke axis. In this mode, the shaft and the piston would be coupled together such that axial movement of the shaft moves the piston along the stroke axis.

A sensor (not shown) indicates to the computer 34 when the plate 46 is in the upwardmost or the initial position. In the illustrated embodiment, the system 10 is oriented such that the stroke axis 52 generally extends vertically; of course, other orientations of the system are also possible.

A lower end of the lead screw 38 is supported by a bracket 25 attached to a bulkhead 26 within the cabinet 24, and an upper end of the lead screw 38 is also suitably supported within the cabinet 24 (although not illustrated in FIG. 1A for simplicity). The lead screw 38 is thereby maintained in a relatively fixed position along the stroke axis 52, and does not move along the axis 52. The lead screw 38, however, is suitably journaled for rotation relative to the supporting structures within the cabinet 24 so as to drive the transfer shaft assembly in the manner described above.

The lead screw 38 also has a sufficient length to define an adequate stroke length of the piston 14. This stroke length desirably includes a first travel range and a second travel range. In the first travel range, the piston 14 slides within the hopper 12 between an initial dispensation step position (in which the piston 14 begins to compress the bag 22) and a final dispensation step position (in which the piston 14 lies next to a bottom wall of the hopper 12). In the second travel range, the piston 14 moves between the initial dispensation step position to a retracted position, in which the piston lies above the hopper 12. These travel ranges are desirably preset and stored in the memory of the motor controller, which is described below.

Seals 54 are placed within holes in the bulkhead 26 and around each transfer shaft 48, 50 in order to seal the pump compartment 30 from the drive mechanism compartment 28.

The motor 36 drives the transfer shafts 48, 50 to move the piston 14 within the first and second travel ranges. At least within the first travel range, in which the piston 14 operates within the hopper 12, the motor 36 moves the piston through a series of sequential dispensation steps between the initial dispensation step position and the final dispensation step position. Each dispensation step corresponds to a distinct dispensation position of the piston 14 within the preset first travel range. The stroke length between each position desirably varies, however, depending upon the fullness of the flexible bag 22, as will be described in detail below.

For this purpose, a motor controller, which forms part of a controller computer 34, operates the motor 36. Any variety of position-controlled motors can be used, for example, servomotors, stepper motors and the like, which are known to those skilled in the art. It is important to note, however, that the stroke length of each dispensation step is not directly related to the step movement of the stepper motor. For example, the motor may be incremented any number of steps in order to move the piston a desired stroke length of one dispensation step. In the illustrated embodiment, the motor is a brushless, DC stepper motor available commercially from Applied Motion Products, of Watsonville, Calif. The motor 36 desirably is controlled by a controller available from Magnon Engineering Inc., of Rancho Cucamonga, Calif. The controller forms part of a computer 34 that can be housed within the cabinet 24. While FIG. 1A schematically illustrates the computer controller 34 within the drive mechanism compartment 28 of the cabinet 24, the computer 34 can also be located outside the cabinet 24 even at a remote location. Although not illustrated, conventional cables connect the computer 34 to the motor, and a suitable DC power supply supplies power the motor 36. The power supply can also be housed within cabinet 24.

The piston 14 is releasably coupled to the ends of the transfer shafts 48, 50. This allows a worker to remove the piston 14 from the cabinet 24 for cleaning. The ends of the shafts 48, 50 desirably include pegs which can be slid into corresponding receiving grooves formed on the upper surface of the piston 14 by moving the piston transversely (i.e., in a direction generally normal to the stroke axis 52). However, other types of releasable coupling, which will be well known to those skilled in the art, can also be used.

The hopper 12 can be formed in a variety of different shapes; however, the hopper 12 desirably includes a generally smooth inner surface without sharp corners (e.g., 90° corners). This structure reduce the likelihood of accidental tearing of the sealed bag and enhances safe handling of the hopper 12. In the illustrated embodiment, as best shown in FIGS. 6–10, the hopper 12 has at least a bottom wall 56 and two elongated side walls 118, 119. End walls 112 interconnect the side walls 118, 119. Each end wall 112 has three panels which abut at obtuse angles with one another and with the corresponding side walls 118, 119. The hopper 12 thus has an elongated octagonal cross-sectional shape, as taken in a plane that lies generally normal to the stroke axis 52. In another form, the hopper 12 has a generally elongated oval shape with a smooth interior surface. This embodiment can be formed by drawing, as is known in the art. The hopper 12 receives a similarly shaped flexible bag 22. In this manner, substantially no air pockets occur between the hopper 12 and the bag 22. In other applications, the flowable material may be loaded directly into the hopper 12, such as in bulk form, so that it is not necessary that the material be contained within a bag.

The bottom wall 56 includes an aperture 58 which is sized and shaped so that the enfitment 18 can protrude into the hopper 12. In the illustrated embodiment, the aperture 58 is generally circular in shape and is formed towards an end of the hopper 12 which normally lies adjacent to the door 41 of the cabinet 24. In this position, the enfitment 18 lies near the front side of the cabinet 24.

The hopper 12 also includes a handle 60 on its front side to facilitate handling of the hopper 12. The hopper thus can be removed from the system to load and reload pre-sealed flexible bags 22 into the hopper or to clean the hopper. The handle 60 can also include one or more slotted holes (FIG. 9) which are designed to interact with a handling tool. This allows a worker to handle the hopper 12 when heated. Additional features of the hopper 12 will be described below in connection with FIGS. 6–10.

At least a face of the piston 14 fits snugly into hopper 12, but may be easily removed for cleaning. For this purpose, at least the face of the piston 14 generally has a cross-sectional shape, as taken in a plane generally normal to the stroke axis 52, that generally matches that of the hopper 12. Thus, in the illustrated embodiment, the piston 14 has a generally uniform cross-sectional shape which is an elongated oval or octagonal shape complementary to the hopper's shape. In this manner, the hopper 12 generally defines an actuation cylinder in which the piston 14 operates. Only minimal clearance occurs between the piston 14 and the hopper 12.

The piston 14 further includes a recess 15 on its face shaped to receive the portion of the enfitment 18 which extends into the bag 22. In the illustrated embodiment, the recess 15 is circular-shaped to receive the circular-shaped piercing member 80 of the enfitment 18. The recess 15 receives the piercing member 80 as the piston 14 reaches the end of its predetermined stroke length, thereby maximizing the amount of material which is dispersed from the bag 22.

With reference to FIG. 1A, the base 16 desirably is removably secured to a bottom floor of the cabinet in the pump compartment 30 for operation, but can be removed for cleaning. In this position, the base 16 lies beneath the hopper 12 and supports the hopper 12 during dispensation of flowable material from the bag 22. Like the bottom wall 56 of the hopper 12, the base 16 also has an aperture 62 which is sized and shaped so that a portion of the enfitment 18 can protrude through the aperture 62 and into the hopper 12. Since the base is generally used for housing a drive mechanism for rotating the enfitment, in some applications, such as when the enfitment is manually attached to the bag, the base 16 is not a necessary component of the system 10.

The base 16 and the hopper 12 can also include interengaging structure that releasably secures the hopper 12 to the base 16 to inhibit relative movement between the hopper 12 and the base 16 when the piston 14 slides within the hopper 12. Such structure can include conventional detent mechanisms which are biased into one or more grooves to hold the hopper 12 to the base 16 by a force greater than the friction force occurring between the piston 14 and the hopper 12 as the piston moves toward the bulkhead 26. The holding force, however, is not so great as to make removal of the hopper 12 from the base 16 difficult.

The enfitment 18 also includes a bearing surface below its upper end. This surface cooperates with the wall of the base aperture 62 to journal the enfitment 18 for rotation. Additional features of the base 16 will be described below in connection with FIGS. 11, 12 and 13.

While both the base 16 and the piston 14 can be constructed from a wide variety of materials, the base 16 and piston 14 in some applications (e.g., food dispensation) desirably are made of a wear-resistant, oxidation-resistant, cleanable material. Suitable materials for such application include, for example, stainless-steel, acetal resin (e.g., DELRIN®), tetrafluoroethylene (e.g., TEFLON®), polytetrafluoroethylene (a.k.a. PTEF), or like polymers.

A portion of the enfitment 18 extends into the hopper cavity by protruding through both apertures 58, 62 in the base and the bottom wall of the hopper, as noted above. One end of the enfitment 18, an end with a piercing member, is positioned to abut the bottom surface of the flexible bag 22. As the piston 14 is initially positioned within the hopper 12, it presses down on the flexible bag 22, thereby compressing the bag between the bottom and side walls of hopper 12 and the piston 14. After the bag is at least slightly compressed against the bottom of the hopper, the enfitment is rotated to pierce a hole in the bag. As is discussed in further detail below, further rotation of the enfitment stretches the bag to enlarge a hole in the bag and simultaneously positions the opening of the bag around the enfitment to seal these components together. An additional seal may be formed between the base 16 and the bottom wall 56 of the hopper 12 by a mechanical O-ring type seal (not shown).

In some applications, an enfitment is not used for dispensation of the material. For instance, a bag may be simply pierced or opened so that the material flows out through the exit nozzle 20. In other instances, the nozzle or the enfitment may be unitary with the flexible-walled container and, therefore, it will not be necessary to puncture the flexible-walled container with a separate enfitment. For example, the enfitment and flexible-walled container may together comprise a replaceable or refillable cartridge, such as those containing caulking, grease, adhesives, etc.

Figure 1B:
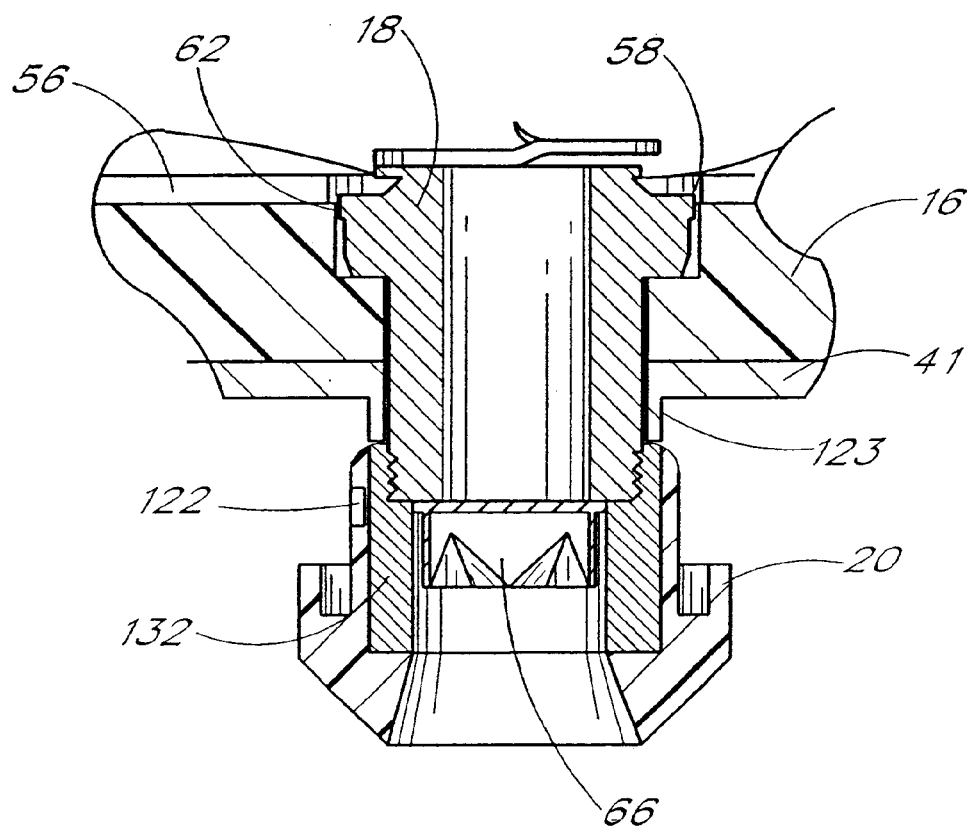
FIG. 1B is an enlarged side cross-sectional view of the enfitment device coupled to the exit nozzle assembly of FIG. 1A.

As illustrated in FIGS. 1A and 1B, an exit nozzle assembly 20 is connected to the end of the enfitment which is not in contact with the bag. The exit nozzle 20 may be made of hard plastic or metal, or both. A pressure-release valve 66 is positioned within the nozzle assembly 20 to selectively permit dispensation of the flowable material from the bag 22. In some applications, the valve is a one-way pressure-release valve. An exit diaphragm 66, preferably made of an elastomer, such as rubber or silicone desirably is used with the valve. The exit diaphragm 66 can have various sized exit slits and be of a suitable durometer rating in order to accommodate a wide range of viscosities of flowable materials. In the illustrated embodiment, the exit diaphragm 66 is a conventional duckbill-type diaphragm; however, a slitted flat disk diaphragm can be used as well. It should be noted that the term "viscosity" is used loosely to refer to the ease at which material can flow or be forced through a passage.

The exit nozzle 20 and the enfitment 18 are interconnected on opposite sides of the cabinet lower wall to releasably secure the base 16 and each other to the cabinet 24. The upper end of the exit nozzle lies just below the lower surface of the cabinet 24 in order to allow the enfitment 18 and nozzle 20 to rotate with minimal friction occurring between these components and the cabinet 24. As assembled, an annular flange on the diaphragm 66 is interposed between a lower end of the enfitment 18 and an inner shoulder on the nozzle 20 to secure the diaphragm 66 in place. Further details of the nozzle assembly 20 are described below in connection with FIGS. 14–16.

Figure 2:
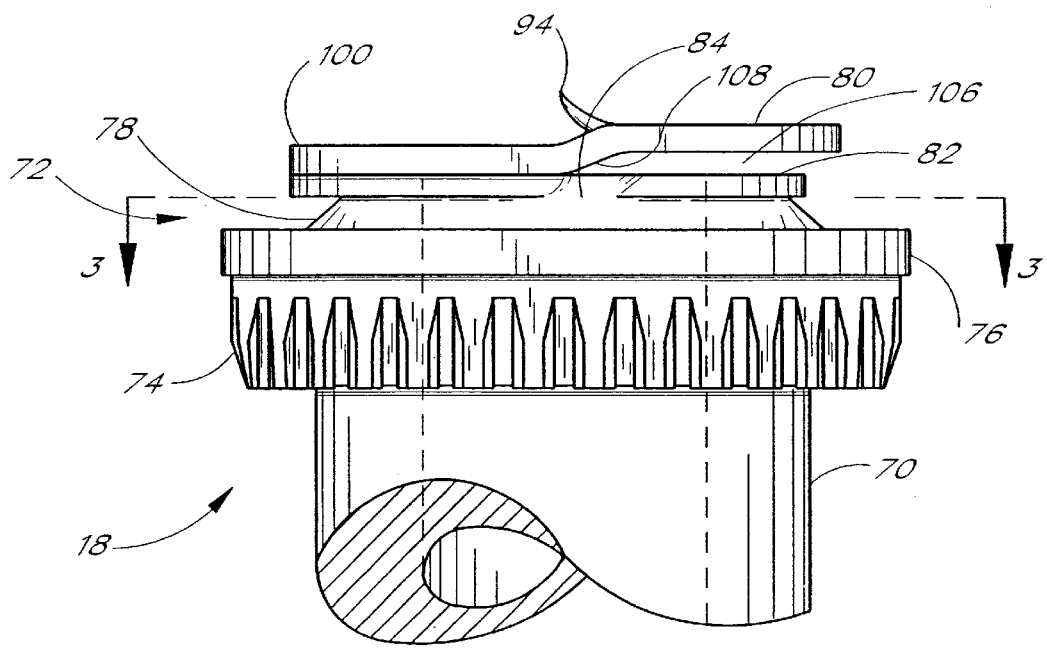
FIG. 2 is a side view of an enfitment apparatus of the present invention.

FIGS. 2–5 illustrate a preferred embodiment of a rotatable enfitment of the present invention. The enfitment 18 comprises a hollow tube 70 and an end piece 72 formed on one end of the hollow tube 70. A piercing member, which is generally identified by reference numeral 80, is attached (e.g., welded) to the end piece 72 to open a hole in the flexible bag 22 and to subsequently stretch open the hole to a size that permits threading of the end piece 72 into the hole, as described below. The opposite end of the enfitment 18 carries an external thread to engage the nozzle assembly 20. Although FIG. 2 shows a cylinder as a preferred embodiment of the hollow tube 70, it will be recognized that the enfitment can also take other shapes, such as multi-sided or oval-shaped. The enfitment 18 also desirably includes a ring of teeth 74 just below the end piece 72 for rotating the enfitment 18, as described below; however, the teeth may be omitted in a manual version of the system 10.

The end piece 72 includes a collar 76 and a hollow, annular conical section 78 interposed between the collar portion 76 and the piercing member 80. The collar 76 is located at a lower end of the end piece 72 and extends radially outward from the outer surface of the hollow tube 70. In the following description of the enfitment 18, the collar 76 will be used as a reference plane, with "upper" and "lower" being used relative to a floor or datum established by this plane.

Figure 3:
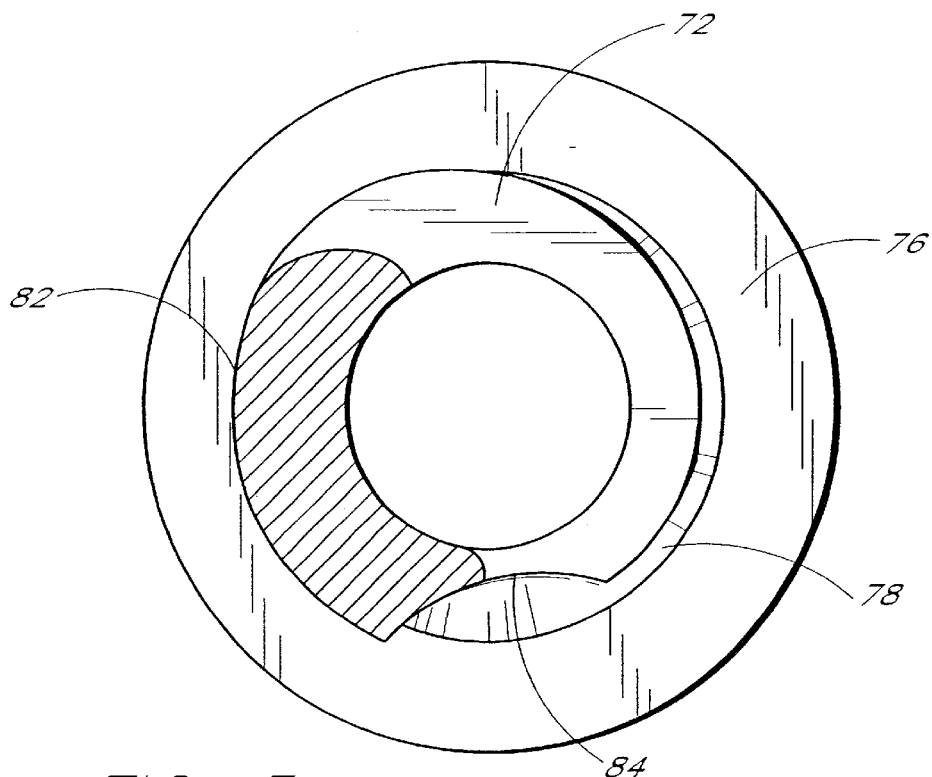
FIG. 3 is a top plan view of the enfitment apparatus of FIG. 2, taken along lines 3—3 of FIG. 2.

With reference to FIGS. 2 and 3, a retaining flange 82 on the end piece 72 extends over at least a portion of the conical section 78 and lies generally parallel to the plane of the collar 76. The degree by which the retaining flange 82 overhangs varies about the circumference of the conical section 78, as best understood from FIGS. 2 and 3 (which illustrate the end piece 72 with the piercing member 80 removed). The hollow conical section 78 and the retaining flange 82 together form part of a sealing device, as described below.

Figure 5A:
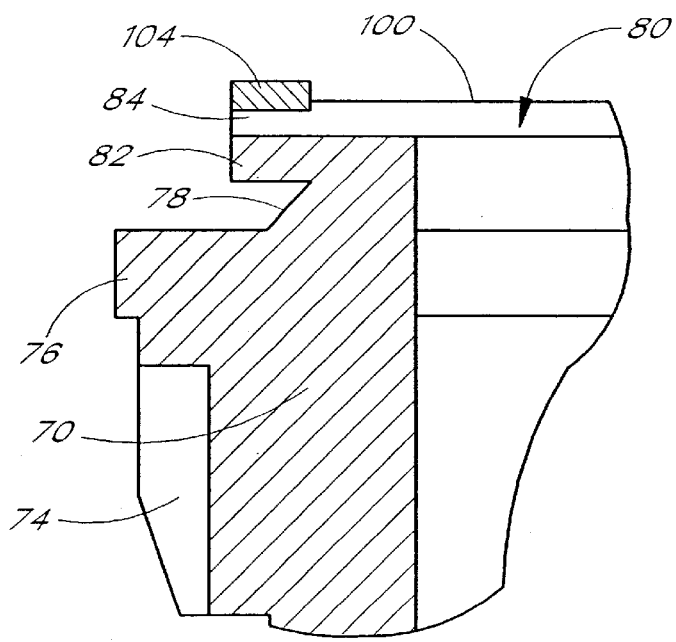
FIGS. 5A and 5B are cross-sectional views of the enfitment apparatus of FIG. 4 as taken along lines 5A—5A and 5B—5B, respectively.
Figure 5B:
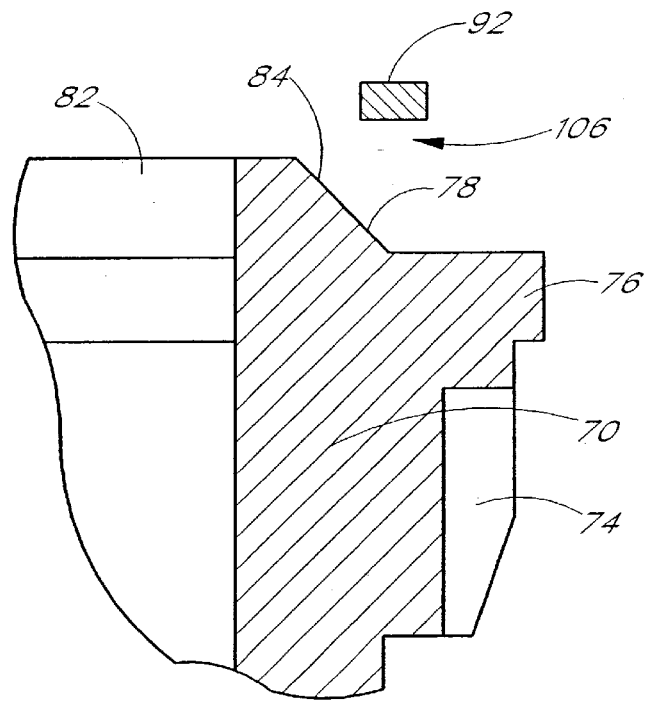

A recessed section 84 also cuts into the retaining flange 82 and forms a smooth transition with the sloped surface of the conical section 78. That is, as best seen in FIG. 5B, at least a portion of the end piece 72, that lies inward of the upper end of the conical section 78 at the recess 84, slopes upward toward the center of the end piece 72 at generally the same incline angle as that of the surface of the conical section 78. This recessed section 84 forms a portion of an unsealing mechanism to permit removal of the enfitment 18 from the bag 22, as described below.

Figure 4:
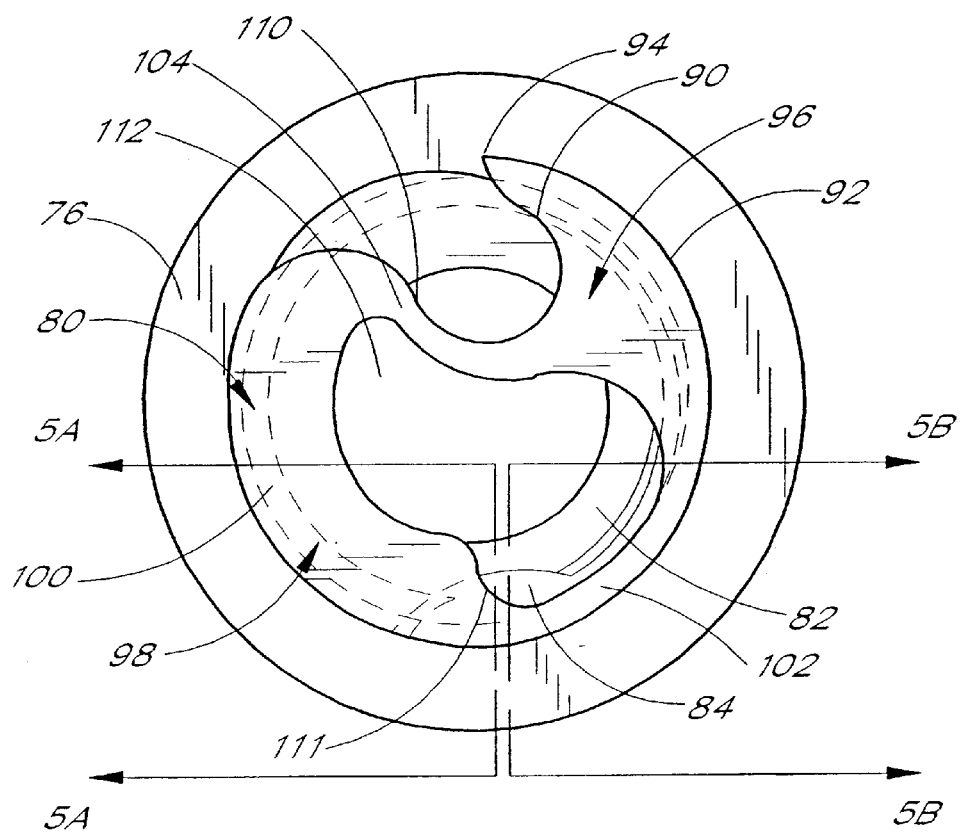
FIG. 4 is a top view of the enfitment apparatus of FIG. 2.

As best seen in FIG. 4, the piercing member 80 desirably includes a leading edge portion 90 and a trailing edge portion 92 that merge together and form the sharp point 94 which bends slightly upward. The leading and trailing edge portions 90, 92 diverge to give this section of the piercing member 80 a sickle-like shape (which is generally designated by reference numeral 96 hereinafter). A curvilinear structure 98 connects together the diverged ends of the leading and trailing edge portions 90, 92.

The curvilinear structure 98 includes a mounting base 100 and a pair of transition sections 102, 104. The mounting base 100 and the first transition section 102, which extends between the trailing edge portion 92 and the mounting base 100, generally extend around an arc, as viewed from above the end piece 72, and substantially follow the outer periphery of a lower end of the conical section 78. As best understood from FIGS. 2 and 3, the mounting base 100 is attached directly atop a portion of the retaining flange 82. FIG. 3 illustrates the foot-print of the mounting base 100 on the retaining flange 82 as a shaded section.

As seen in FIG. 2, the transition sections 102, 104 support the leading and trailing edge portions 90, 92 (i.e, the sickle-like portion 96 of the piercing member 80) above an upper surface of the retaining flange 82. A gap 106 thereby exists between the retaining flange 82 and the portion of the piercing member 80 which includes the sharp point 94. As best seen in FIGS. 2 and 5B, an upstanding surface 108 of the transition section 102 defines one end of the gap 106 at a point between the mounting base 100 and the recessed section 84 in the retaining flange 82. In this position, the upstanding surface 108 lies approximately 180° around the circumference of the piercing member 80 from the sharpened end 94.

With reference to FIG. 4, the second transition section 104 and the leading edge portion 90 together form an inwardly extending loop that reduces a distance between the leading and trailing edges 90, 92 over at least a section of the circumference of the piercing member 80. That is, the leading edge portion 90 extends inward while gradually tapering away from the trailing edge to a point 110. From that point, the transition section 104 connects the leading edge portion 90 to the mounting base 100.

An aperture 112 is formed in a center section of the piercing member 80 between mounting base 100, the transition sections 102, 104 and the leading and trailing edge portions 90, 92. The aperture 112 communicates with the inner space within the hollow conical section 78, which in turn is connected to the tubular body 70. In this manner, the flowable material within the bag 22 can pass through the piercing member 80 and the end piece 72 of the enfitment 18 and into the tubular body 70 of the enfitment 18. The opposite end of the tubular body 70 communicates within the nozzle assembly 20, as described above.

FIGS. 6–10 illustrate the hopper or container 12 for holding the bag 22 of flowable material. In addition, to the above-noted features, the hopper 12 includes a longitudinal slot or groove 120 in the bottom wall 56 of the hopper which extends at least partially from the front to back walls of the hopper 12. Additional slots or grooves in the bottom wall of the hopper 12 can also be located along the front and back sides of the hopper to channel the contents of the plastic bag 22 toward the hopper opening 58 for dispensation. Thus, the amount of material dispensed from the bag 22 is maximized and very little flowable material is wasted. In addition, these slots allow water to drain from the hopper 12 during cleaning.

As illustrated in FIGS. 6–9, a plurality of piston guides 114 extend from the top of the hopper walls. Each piston guide 114 extends upward from the wall of the hopper with a upper end bent inward over the cavity of the hopper 12. When the hopper is installed within the system 10, the piston 14 is positioned between the hopper cavity and the bent ends of the piston guides 114. In this manner, the user can easily slide the hopper 12 into place just below the piston 14 by using the piston guides 114. The hopper 12 remains suspended until it is desired to engage the hopper 12 with the enfitment 18.

At least one of the piston guides 114 can include a hook 116. A worker can use the hook 116 to pre-puncture the bag 22 before insertion into the hopper 12, if needed.

Figure 11:
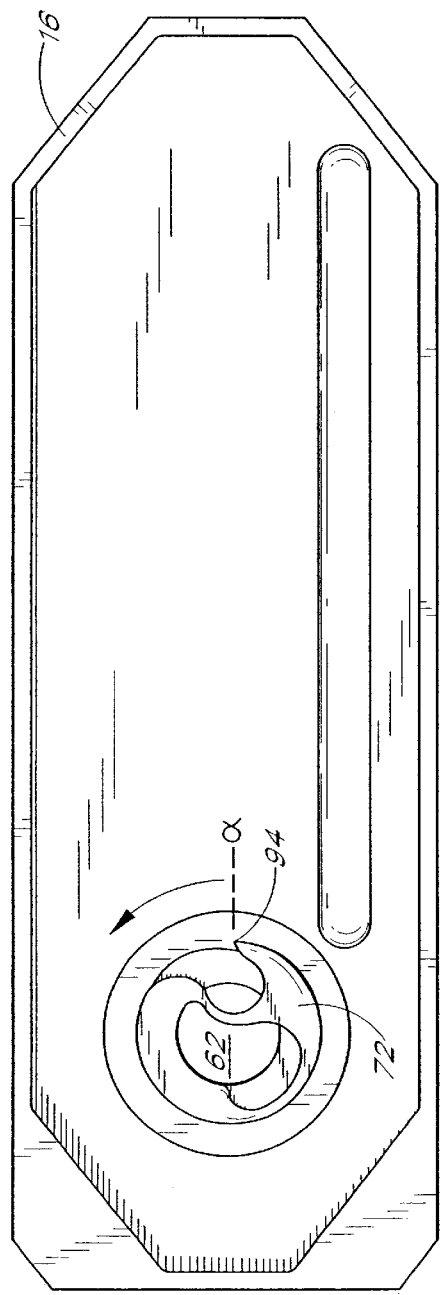
FIG. 11 is a top plan view of the enfitment apparatus of FIG. 2 within an opening in a base of the system illustrated in FIG. 1A, with the enfitment positioned in a desired initial position for one application.
Figure 12:
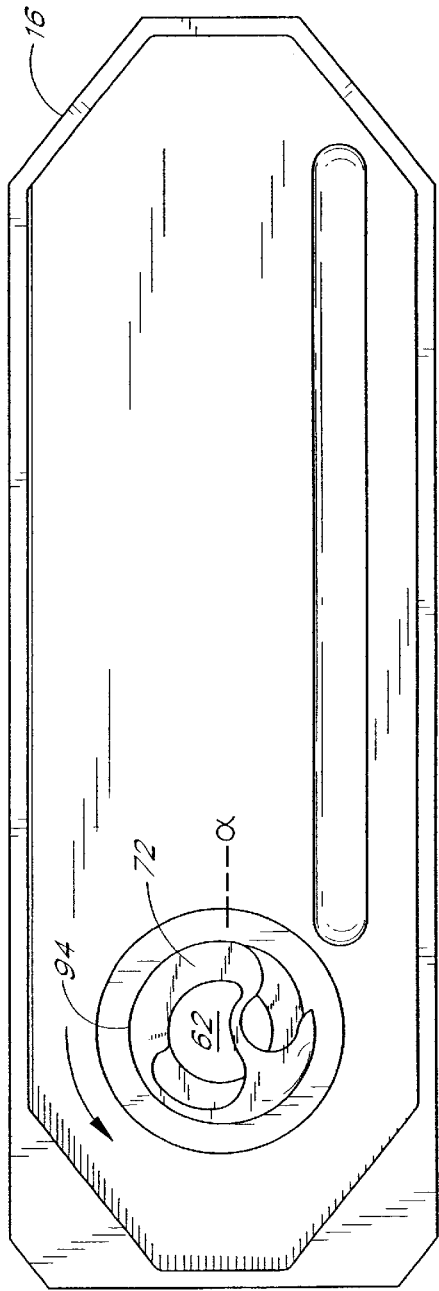
FIG. 12 is a top plan view of the enfitment apparatus and base assembly of FIG. 11 with the enfitment in an initial position for another application.

FIGS. 11 and 12 show a top view of the base 16 with the end piece 72 of the enfitment 18 inserted through the base aperture 62. The enfitment 18 can be initially positioned with the sharp point 94 at any location. FIG. 11 illustrates the position of the enfitment 18 within the base prior to placement of the hopper over the base ($\alpha=0°$), such that the enfitment is in a desired initial position for certain applications. In this position, the enfitment 18 will stretch a lower surface of the bag 22 by pulling against the largest area of the bag's surface areas about the enfitment 18. In certain instances, if the enfitment 18 does not begin to stretch the bag 22 from this location, the enfitment 18 may tend to pull the corresponding side of the bag 22 down, which can cause the enfitment 18 to twist and tear the bag 22. In other instances, however, it is desirable to position the enfitment 18 at a position other than that shown in FIG. 11. FIG. 12 shows another initial position of the enfitment 18 for use in other applications, such as when the bag has thick seams or excess plastic along the center seam of the bag 22. By starting at the location illustrated in FIG. 12, the enfitment 18 will be able to dig into the bag 22 so that the piercing member 80 can puncture the bag 22. It is noted that by controlling the starting position of the enfitment 18, the enfitment 18 can be positioned in any desirable starting position to avoid a seam, a seal, or other item which might interfere with the opening of the bag 22.

A sensor can be used to ensure that the enfitment 18 is in the desired initial position prior to engaging the bag 22 with the enfitment 18. In the illustrated embodiment, as best seen in FIG. 1, the sensor comprises a Hall-effect transducer 121 that interacts with a magnet 122 embedded in an exterior wall of the nozzle 20. The Hall-effect transducer 121 generates a signal which is input to the computer controller 34. The computer 34 uses this signal to control the position of the enfitment 18, in the manner described below.

Figure 13:
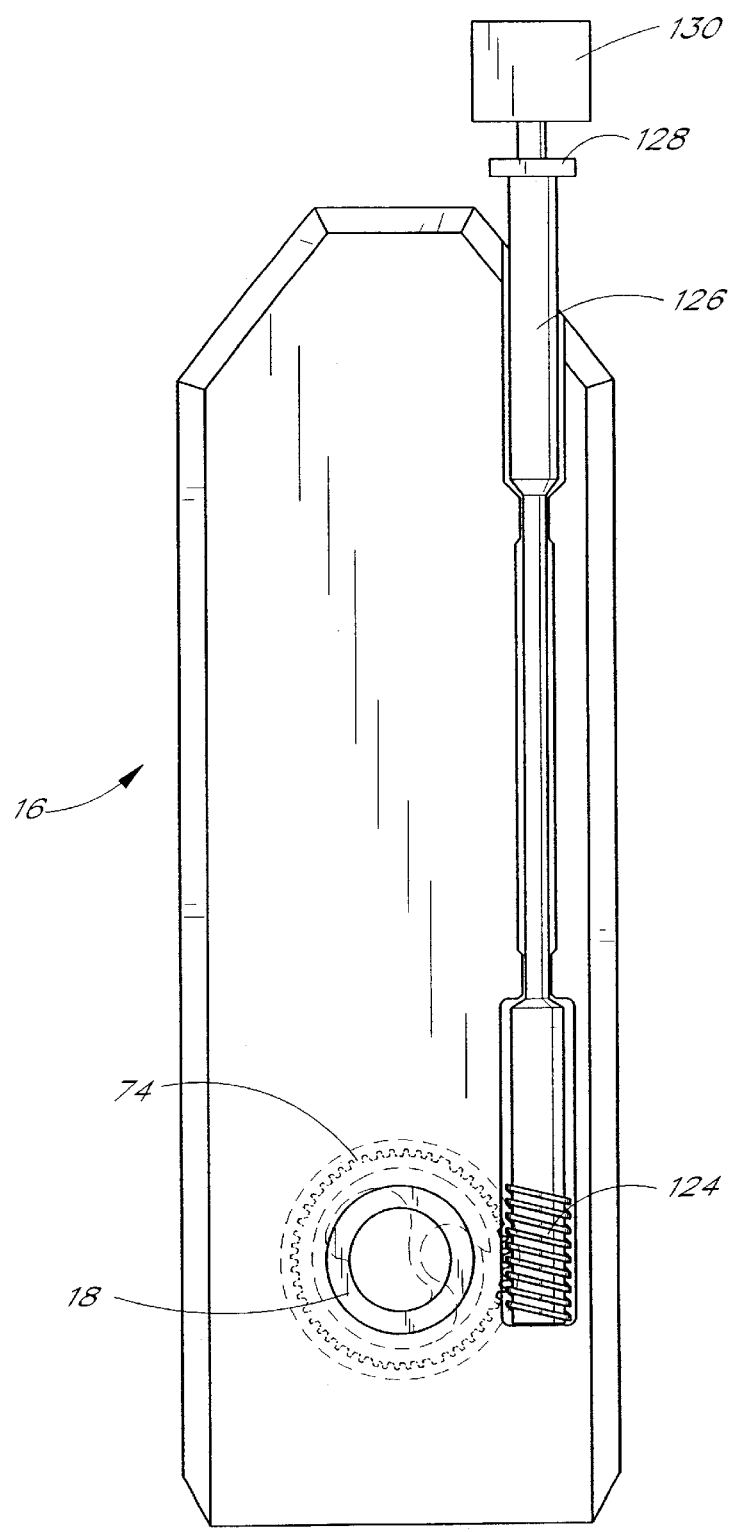
FIG. 13 is a bottom view of the base illustrated in FIG. 11 showing the enfitment (in phantom) and drive mechanism for rotating the enfitment.

FIG. 13 shows a bottom plan view of the enfitment 18 (apart from the nozzle assembly 20) and the base 16 as used with motorized version of the present dispensation system. The cabinet 24 and the other support structure have not been shown in order to simplify the drawing. The enfitment 18 is positioned adjacent a gear assembly so that the teeth 74 of the enfitment can be rotated by a drive mechanism including a worm gear 124. The interaction between the enfitment teeth 74 and the worm gear 124 rotates the enfitment 18 counterclockwise from an initial position to a sealed position within the bag 22. Reverse direction of the worm gear 124 unthreads the enfitment 18 out of the bag 22 in the manner described below.

A positioned controlled motor 130 connects to a shaft 126 through a coupler 128. Since the teeth 74 of the enfitment 18 are in contact with the worm gear 124, as the shaft 126 is rotated by the motor 130, the worm gear 124 rotates the teeth 74 of the enfitment 18. this manner, the enfitment can be automatically rotated by the motor 130.

The motor 130 desirably lies outside the pump compartment 30; however, it need not be positioned outside the cabinet 24 as illustrated. While any variety of position-controlled motors can be used, the motor 130 desirably is a DC brushless stepper motor, available commercially from Applied Motion Products, of Watsonville, Calif. A controller, which is desirably part of the computer 34, also desirably controls the motor to precisely control the rotation and position the enfitment 18. A suitable controller is available from Magnon Engineering Inc., of Rancho Cucamonga, Calif. A conventional cable interconnects the computer 34 to the motor 130, and power is supplied to the motor 130 by the DC power supply, as described above in connection with the pump motor 36. It is, of course, possible to rotate the enfitment 18 manually so that the motor 130, the worm gear 124, the shaft 126, the coupler 128 and even the teeth 74 of the enfitment are not needed.

Figure 14:
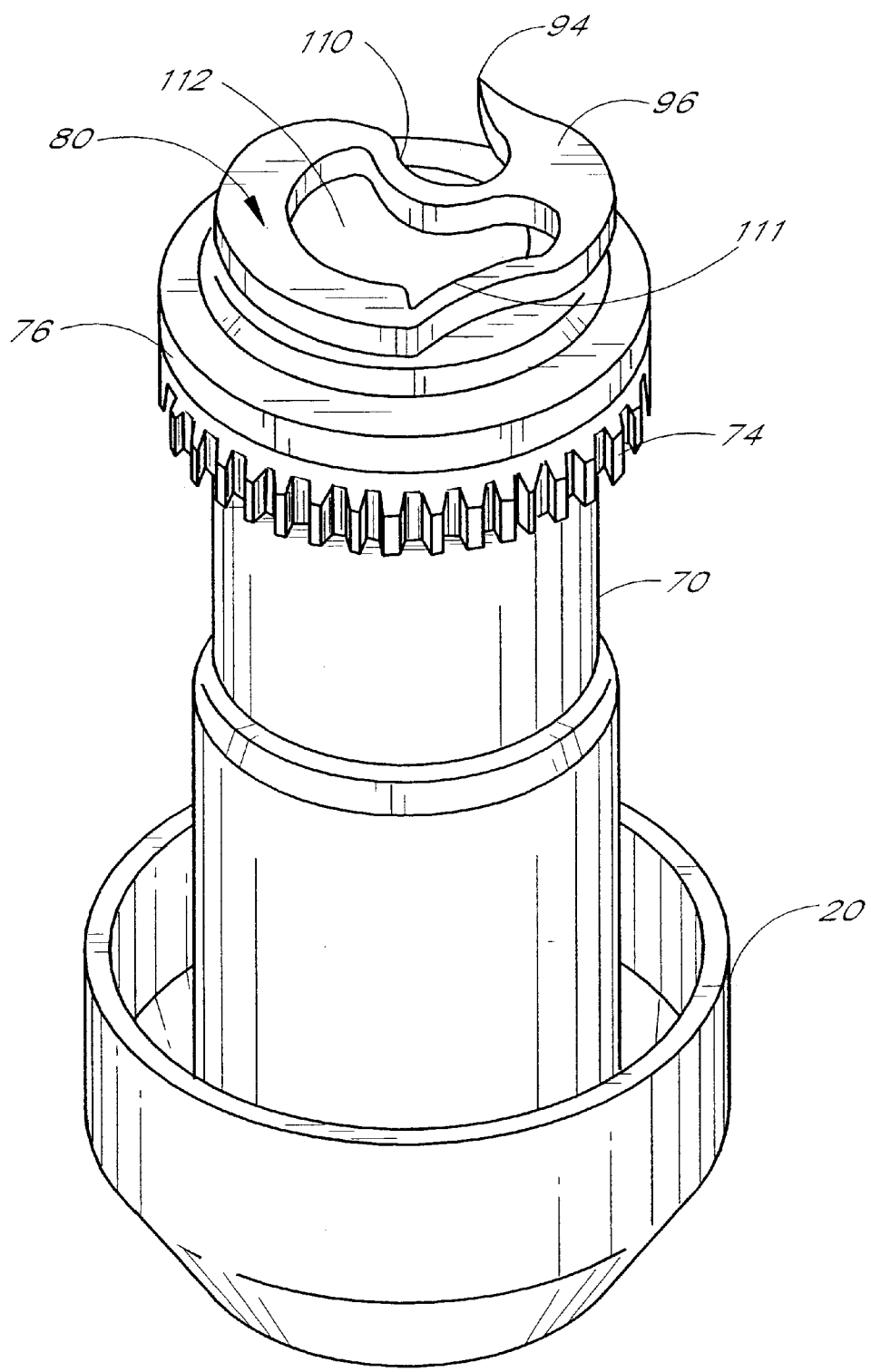
FIG. 14 is a perspective view of a preferred embodiment of the enfitment device of the present invention coupled to an exit nozzle assembly.
Figure 15:
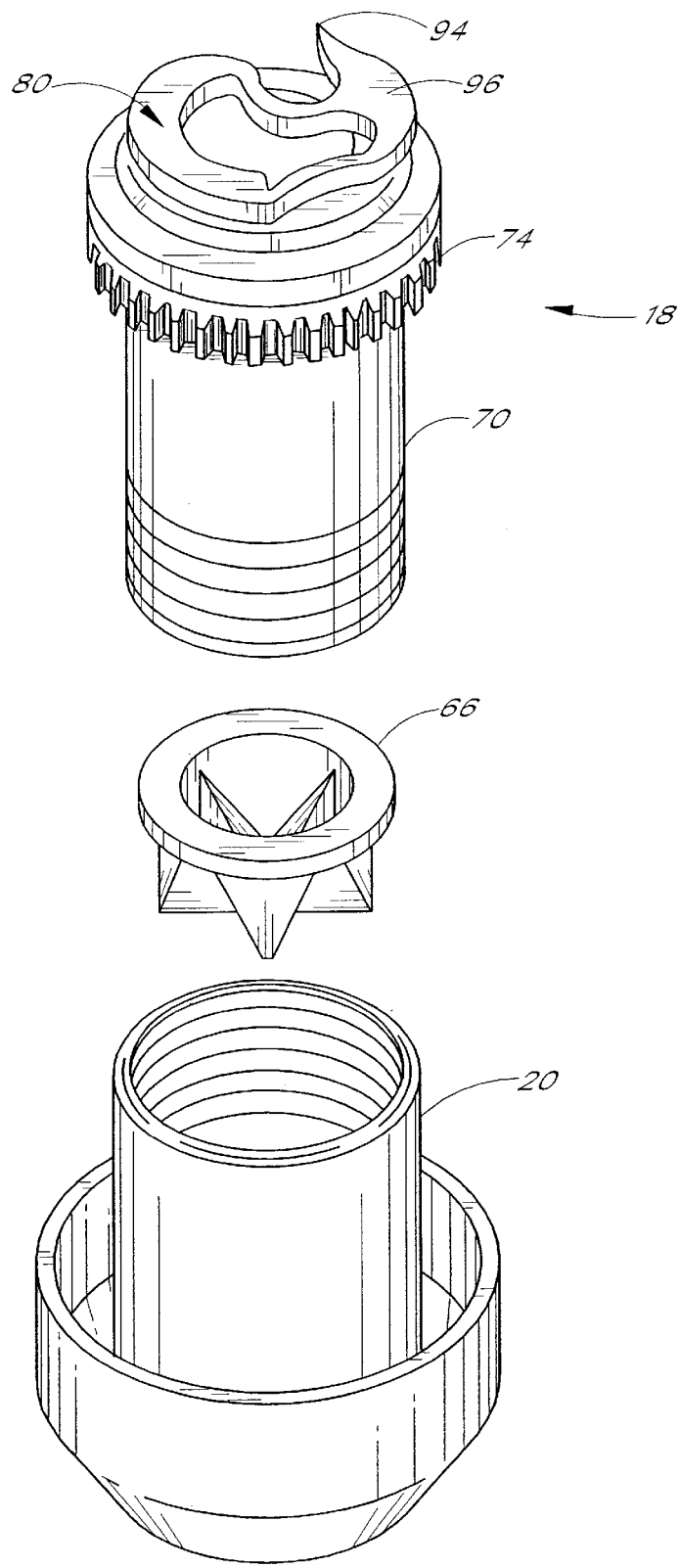
FIG. 15 is an exploded perspective view of the embodiment of FIG. 14, showing the split diaphragm separated from the exit nozzle.
Figure 16:
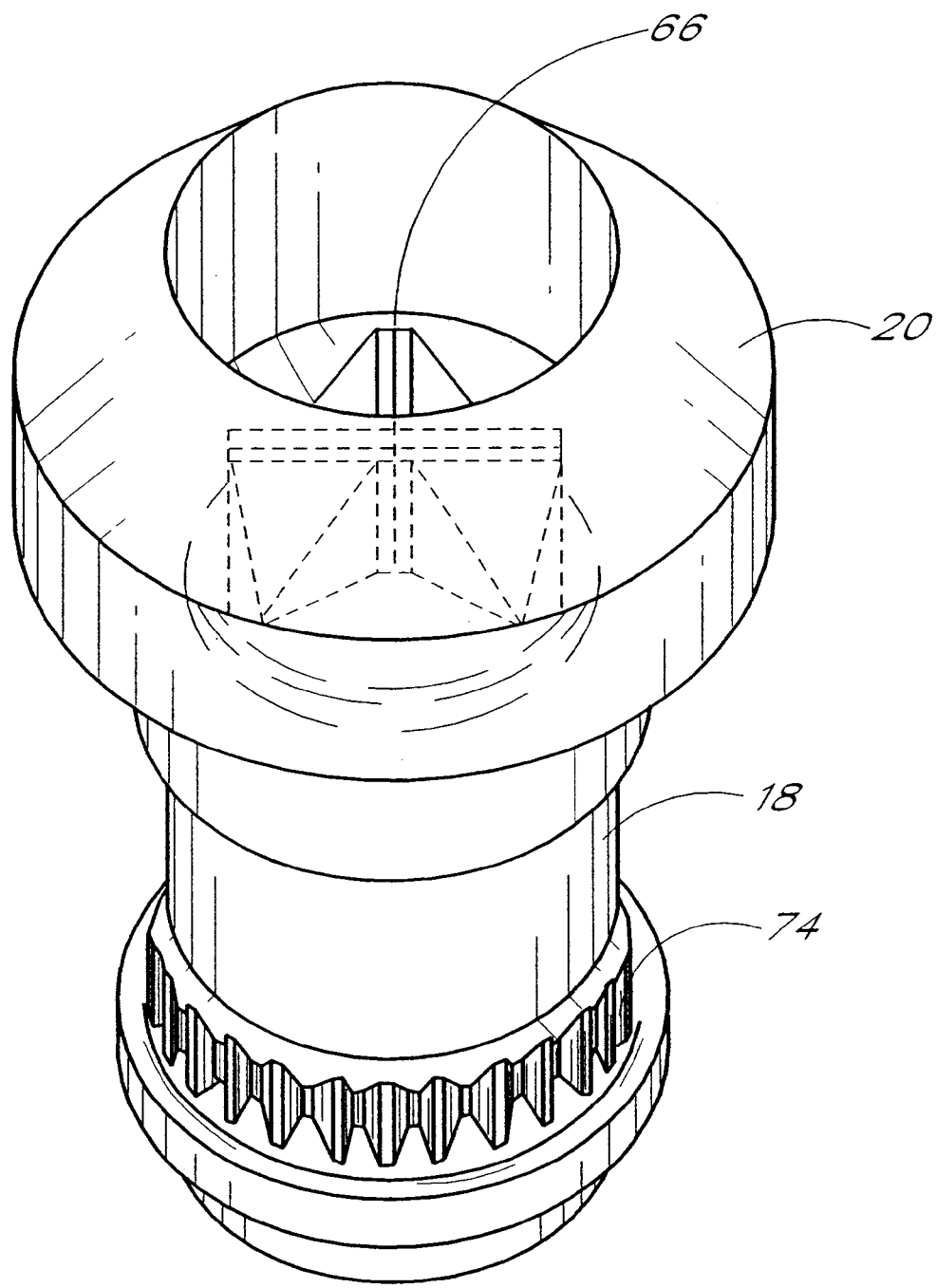
FIG. 16 is an inverted perspective view of the assembly of FIG. 14, showing the split diaphragm in phantom within the exit nozzle.

With reference now to FIGS. 14–16, the hollow tube 70 of the enfitment apparatus 18 is coupled to an exit nozzle assembly 20. FIG. 15 is an exploded perspective view of the enfitment 18, the exit diaphragm 66 and the exit nozzle 20, with the exit diaphragm 66 separated from the exit nozzle 20. The exit diaphragm 66 has at least one slit or aperture through which the material may be dispensed. The slit may vary in size, but is preferably between ⅜ of an inch to 1 inch in length. The slit of the exit diaphragm self-seals in the absence of pressure on the diaphragm. Thus, the flowable material can be pushed through the diaphragm 66 with relatively little pressure, yet the diaphragm will not leak in the absence of pressure.

In the illustrated embodiment, the exit nozzle 20 includes a threaded counterbore which receives a threaded end of the enfitment 18. When coupled together, such as by screwing the pieces together, the enfitment 18 and the exit nozzle assembly 20 form a leak-proof seal. The exit nozzle 20 acts as a nut to retain the enfitment in place. In this manner, the enfitment 18 is retained so that during operation of the system 10, the enfitment 18 does not move along the stroke axis 52. Further, the exit nozzle 20 attached to the enfitment 18 retains the enfitment 18 so that the teeth of the enfitment are held in operational contact with the worm gear. After placement of the diaphragm 66 in the nozzle 20, the diaphragm 66 is maintained in a sealing engagement by the threaded portion of tubular member.

The system 10 may include multiple nozzles to dispense flowable material from the bag 22. The nozzle or nozzles may be configured in a variety of different ways, such as a goose-neck nozzle or for remote use. A remote nozzle can comprise flexible tubing attached to the enfitment with the nozzle attached at the other end. A goose-neck nozzle is desirable in certain applications, such as when upward movement of the piston presses the flowable material from the top of the bag and through the exit nozzle. A remote nozzle may be manipulated by the user to a dispense the material to a variety of different locations.

In order to maintain the temperature of the flowable material within the enfitment and nozzle assembly with a controlled temperature range, the exit nozzle assembly 20 is preferably either made at least in part of a material which conducts heat or is lined with such a material. With reference back to FIGS. 1A and 1B, heat is transferred to or away from the temperature-controlled compartment to the cylindrical tube 132 within the nozzle 20 via the enfitment 18 and the flowable material within the bag 22. In a preferred embodiment, the exit nozzle 22 is made in part of an insulating material (e.g., DELRIN®) surrounding a thermally conductive material 132, such as an aluminum alloy or another similar metal conductor. In this way, material within the exit nozzle 20 can be maintained at a desired temperature.

Alternatively, the nozzle 20 can include one or more internal passages through the body of the nozzle. These passages communicate with the interior of the pump compartment 30, which is maintained at a desired temperature, as noted above. Air from the compartment 30 flows through the air passages to transfer heat either to or from the body of the nozzle 20. That is, when the air within the pump compartment 30 is heated, the hot air will transfer heat principally through convection to the nozzle body. However, when the air within the pump compartment 30 is cooled, flow of cool air acts as a heat sink, and thermal energy is principally conveyed through convection to the air flow from the nozzle body in order to cool the nozzle 20. The nozzle 20 discharges the air at a point below the diaphragm 66.

In addition to the methods of transferring heat toward or away from the nozzle 20, as described above, heat can be transferred through a lip portion 123 of the cabinet 24 extending from the cabinet aperture to the thermally conductive material 132 in close proximity with the cabinet 24. That is, the cabinet 24 and the conducting insert 132 are separated by a slight distance so as not to inhibit the rotation of the enfitment 18, yet small enough to transfer heat between the cabinet 24 and the conducting insert 132. Although in one embodiment, the enfitment 18 is made of stainless steel, the enfitment 18 can be made of other types of material, including, but not limited to aluminum which has been treated for added strength for the enfitment 18.

FIG. 16 shows an inverted exit nozzle assembly 20 coupled to the enfitment 18. The slits of the exit diaphragm 66 are shown in phantom. The illustrated embodiment shows a duckbill diaphragm. Of course, as mentioned above, other types of pressure-release valves can be used.

Operation

A worker initially loads a full flexible bag 22 containing the flowable material into the hopper 12. In some applications, it is advantageous to form a small hole in the bag 22 near its upper end before loading into the hopper in order to remove excess air from the bag 22. The worker can make a hole using the hook 116 that is formed on one of the guides 114. A small hole is not always required prior to dispensation, such as with bags that are vacuum-sealed containing material maintained under refrigeration conditions.

The worker subsequently opens the door 41 of the cabinet 24 and inserts the hopper 12 into the pump compartment 30 of the cabinet 24. In doing so, the hopper 12 is initially hung on the piston 14 using the piston guides 114 as described above. The door 41 is then shut and the motor 36 lowers the piston 14 which causes the hopper 12 to engage the base 16. Continued movement of the piston 14 from its retracted position moves the piston into contact with an upper surface of the flexible bag 22, as illustrated in FIG. 1, i.e., the piston 14 moves into its initial dispensation step position.

When assembled, the raised sickle section 96 of the enfitment apparatus 18 extends through the apertures in the base 62 and the hopper 58 and extends into the cavity of the hopper 12. The other end of the enfitment 18 is coupled to the exit nozzle assembly 20, which includes a diaphragm to control the output of the flowable material. With the piston 14 lowered into its initial dispensation position, the lower flexible wall of the plastic bag 22 lies in physical contact with the enfitment 18.

Upon rotating the enfitment 18 counter-clockwise the point 94 of the enfitment 18 pierces the bottom surface of the elastic bag 22, thereby making a small hole at the original site of penetration. The small hole forms both inner and outer edges 22a, 22b, respectively, separated by the sharpened end 94. The wall of the elastic bag 22 is comprised of a material with sufficient flexible so as to be stretched substantially across the diameter of the enfitment assembly 18, as described below. Although in the illustrated embodiment, the enfitment 18 is rotated in a counterclockwise to puncture the bag and clockwise to unseal the bag, it is also possible to configure the enfitment 18 in such a manner that clockwise rotation punctures the bag and counter-clockwise rotation of the enfitment unseals the bag.

Figure 17A:
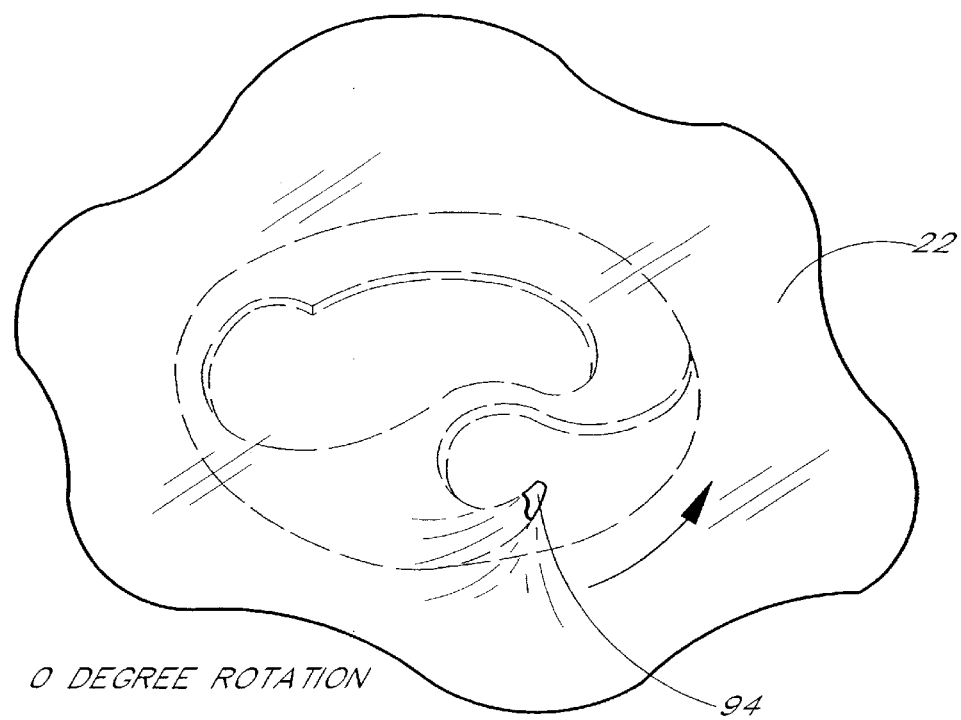
FIGS. 17A–17F illustrate the sequence of opening a flexible-walled container and stretching the opening of the bag around an edge of the enfitment apparatus.

FIGS. 17A–17F illustrate the sequence of opening the flexible bag 22 and wrapping the opening around the enfitment's conical section 78 below the retaining flange 82 to form a seal between the bag 22 and the enfitment 70. FIGS. 17A–17F are viewed from the top looking through a generally stationary bag, with the enfitment 18 rotating counterclockwise. The sequence starts with the piercing end 94 of the enfitment 18 at a 0 degree position with only the piercing tip 94 of the enfitment protruding through the plastic bag 22, as illustrated in FIG. 17A. The purpose of approximately the first 180 degrees of rotation of the enfitment 18 is to open and stretch a hole in the bag 22 so that the further rotation wraps the hole around the enfitment 18 and does not cause the bag 22 to twist. As the enfitment 18 rotates, the bag 22 is stretched across the raised sickle-like section 96 between the leading and trailing edges 90, 92.

Figure 17B:
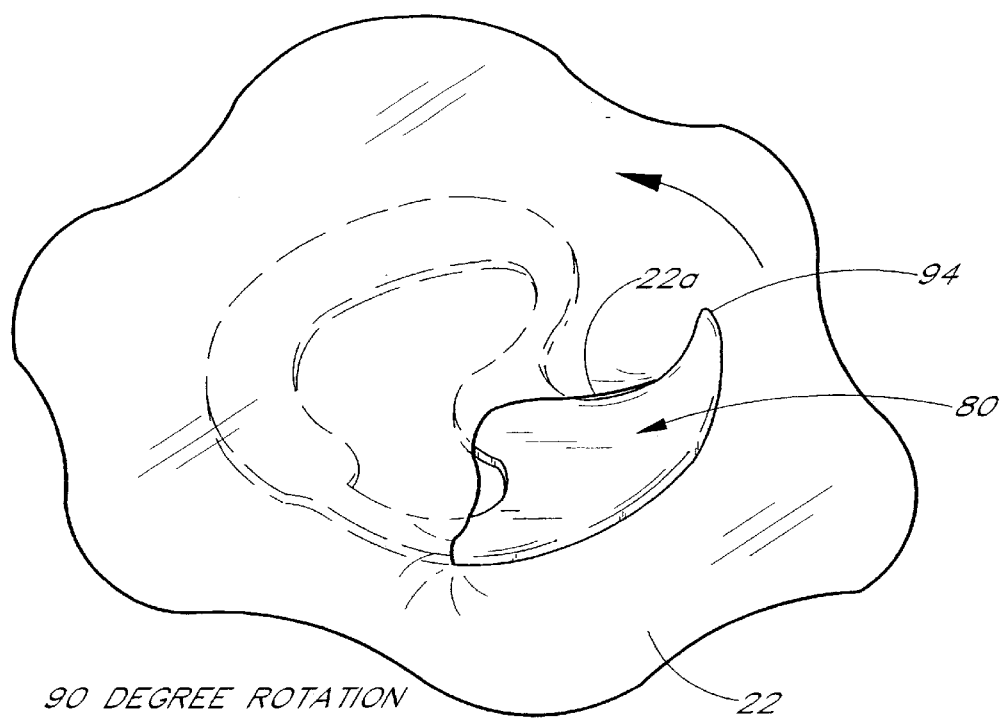

At 45 degrees of rotation, a small hole is opened in the bag 22 by the point 94 on the enfitment 18. The inner edge 22a of the hole extends over an upper surface of the raised sickle section 96 and the lower edge 22b extends below the sickle section 96 and through the gap 106 formed between the retaining flange 82 and the sickle section 96. As illustrated in FIG. 17B, this hole gets pre-stretched around the leading portion of the sickle section 96 of the enfitment 18 at 90 degrees. At 135 degrees the hole in the plastic bag is further expanded.

Figure 17C:
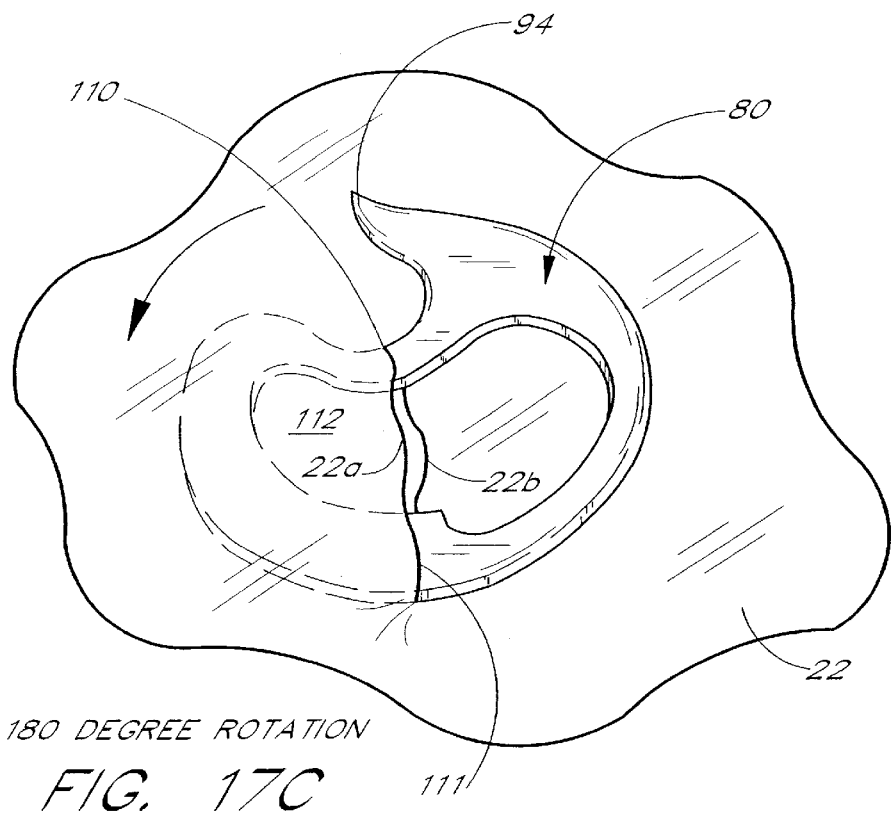

The first substantially 180 degrees of rotation represents a pre-stretching phase. As the enfitment 18 rotates, the bag 22 is stretched across the raised sickle section 96 from location 110 to location 111. This pre-stretching is necessary to reduce the peak torque on the flexible bag 22 to prevent the flexible bag from twisting. Pre-stretching, however, is not necessary for smaller enfitments that open small holes. At location 110, the upstanding surface 108 inhibits further relative rotation between the sickle section 96 and the adjacent bag 22. The downward slope of the surface 108 also forces the bag 22 under the retaining flange 82. As illustrated in FIG. 17C, at about 180 degrees the hole is pre-stretched to its maximum size as about half of the raised sickle section 96 protrudes through the opening being formed in the plastic bag 22.

As the enfitment 18 is further rotated, the flexible bag 22 is forced around the conical section 78 beneath the retaining flange 82. The collar 76 and the conical shape of the above section 78 help prevent further axial migration of the bag 22 along the length of the enfitment 18. The flexible bag 22 is thus stretched around the conical section 78 to form a smooth, generally uniform seal.

Figure 17D:
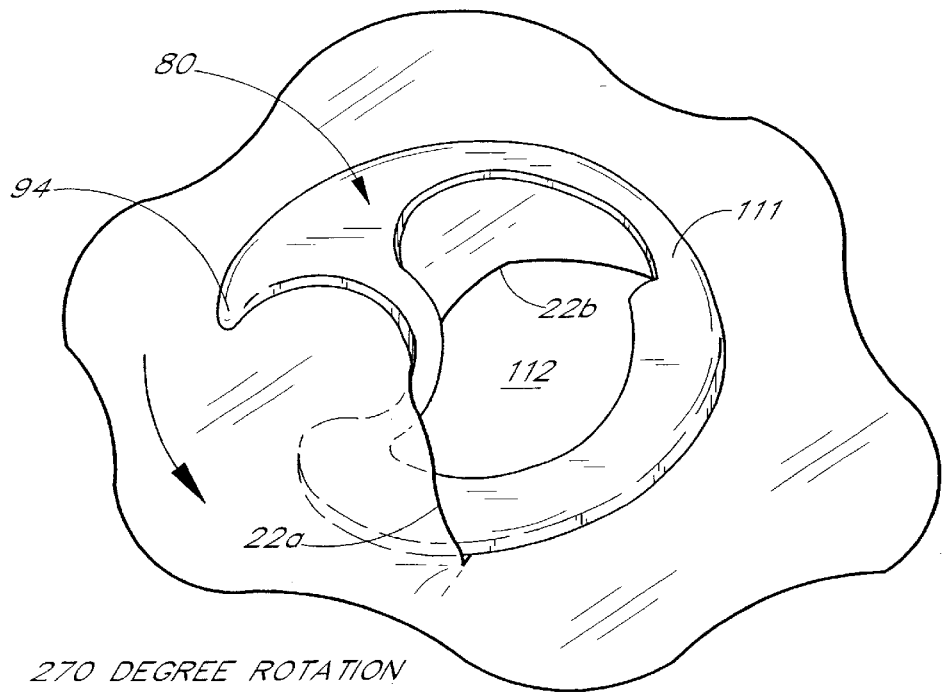

As shown in FIG. 17D, at about 270 degrees, the wall 108 begins to force the outer edge 22b of the hole around the outer edge of the end piece 72, i.e., around the portion of the conical section 78 that trails the wall 108. Through this process, the wall 108 rides over the edges 22a, 22b, and does not significantly torque or pull the flexible material of the bag 22. The opening, however, is further stretched around the end piece 72 as the enfitment 18 continues its rotation.

Figure 17E:
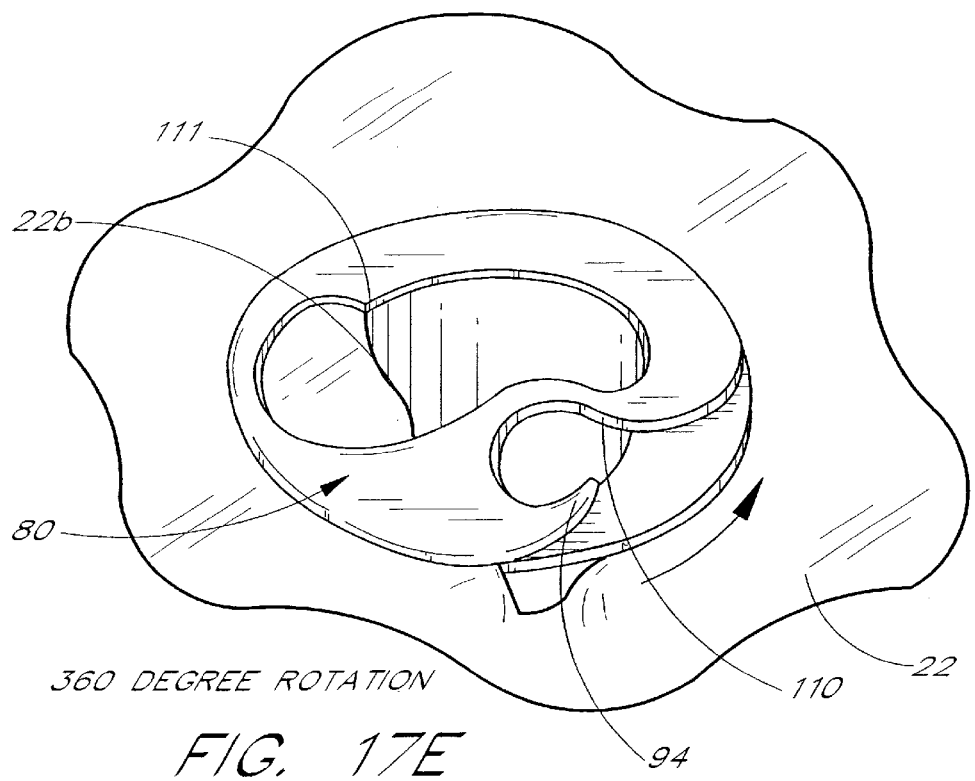

With reference to FIG. 17E, the bag opening is about 75% completely stretched about the conical section 78 of the enfitment 18 is at about 360 degrees. The sharpened point 94 reaches and begins to pass the original site of penetration. Because of its upwardly turned orientation, however, the sharpened point 94 tends not re-pierce the bag 22. The downwardly sloped surface 108 continues to force now the inner edge 22a of the opening beneath the retaining flange 82 and around the conical section 78. Further rotation continues this action of the forcing the opening's inner edge 22b around the conical section 78 of the end piece 72.

Figure 17F:
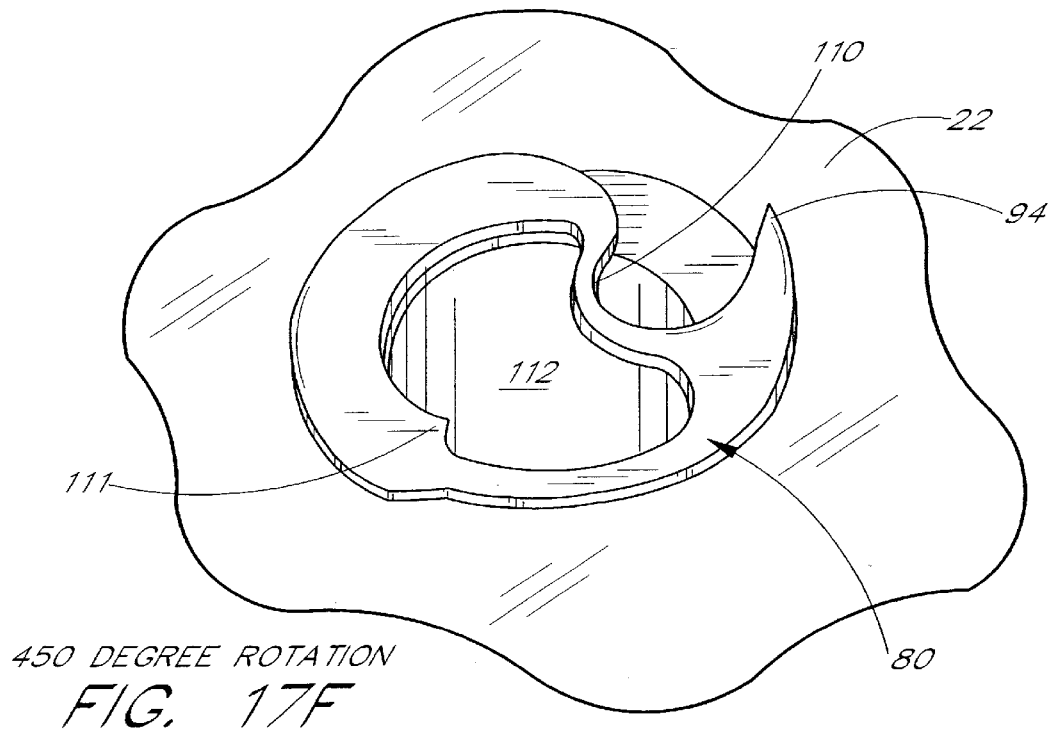

At about 450 degrees the bag 22 has been almost fully wrapped around the enfitment 18, and at about 495 degrees, as illustrated in FIG. 17F, the operation is complete with the bag fully wrapped around the conical section 78 of the enfitment 18. As the enfitment 18 rotates to its final position, the raised sickle section 96 extends into the bag 22. The flowable material in the bag can then flow through the piercing member aperture 112 into the hollow tube 28, through the diaphragm 66, and out the exit nozzle 20.

To detach the flexible bag 22 from the enfitment 18, the enfitment 18 is simply rotated in a direction opposite that which is used to puncture and seal the flexible bag 22 with the enfitment 18. When a seal is formed between the enfitment 22 and the flexible bag 22, a wall of the flexible bag 22 is constrained generally around a conical surface 78 and retained by retaining flange 82, as described above. As the enfitment 18 is rotated in the opposite direction, the conical section 78, which tends to force the bag 22 upwards toward the retaining flange 82, is allowed to rise into the open gap 106. As the enfitment 18 is further rotated in this direction, the bag 22 is unwound from the enfitment 18. In particular, at location 110 on the end piece 72, the recessed section 84 of the end piece 72 guides the bag 22 upward into the gap 106, that is formed between the raised sickle section 96 and the retaining flange 82, and away from the conical section 78. Upon further rotation of the enfitment in this opposite direction, the remainder of the opening's edge rides upward and over the recessed section 84, and off the end piece 72 until the flexible bag 22 is completely disengaged from the enfitment 18. FIG. 5A shows the cross-section of the enfitment 18 as encountered by the bag 22 when the enfitment 18 is rotated counterclockwise, such that the bag is forced under the retaining flange 82. FIG. 5B shows the cross-section of the enfitment 18 at the same area as FIG. 5A, except from a viewpoint of the bag as it is rotated in a clockwise rotation. Here, the bag 22 is pushed up by the slope of the conical section 78 into the gap 106.

Figure 18:
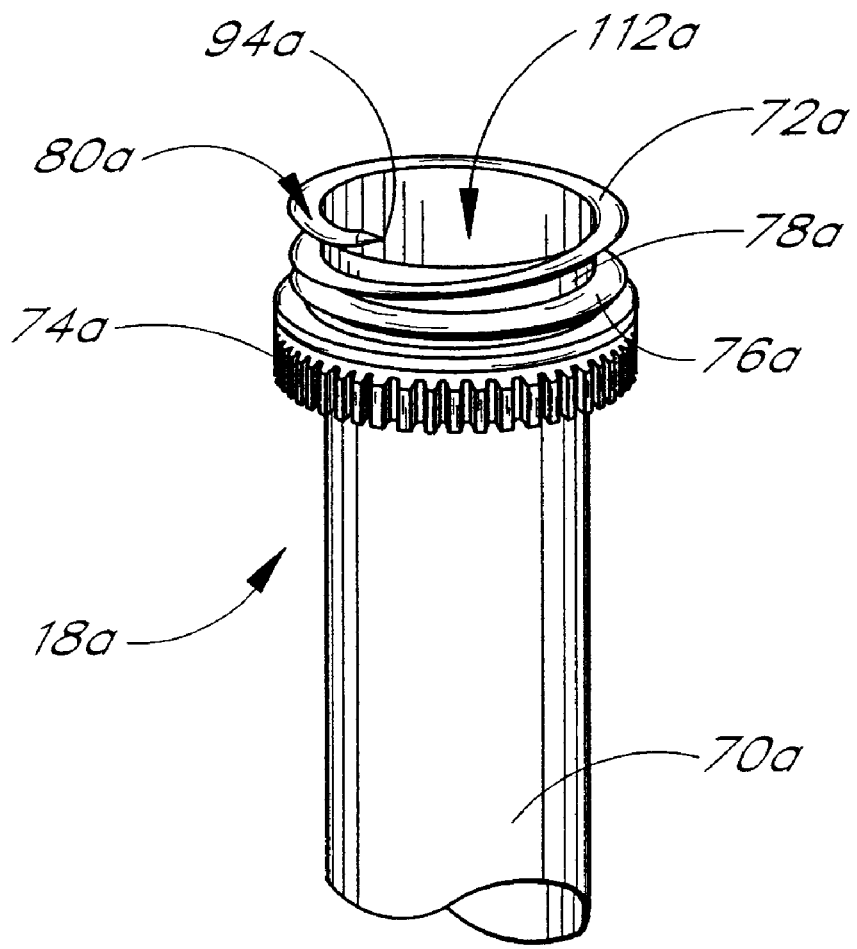
FIG. 18 illustrates an alternate embodiment of the enfitment apparatus of the present invention.

FIG. 18 shows another embodiment of the enfitment of the present invention, with like components being designated by the same reference numeral with an "a" suffix. The enfitment 18a shown in FIG. 18 has a reduced size, including having a reduced diameter hollow tube 70a and end piece 72a. Due the smaller size of the enfitment, it is not necessary to pre-stretch the wall of the bag for forming a smaller hole. Similar to the enfitment of the above-described embodiment, the enfitment of this embodiment has a hollow tube 70a and an end piece 72a having a collar portion or flange 76a. Because the smaller enfitment does not pre-stretch the bag, the end piece is simplified. For instance, surface 78a does not have to be conical shaped; instead, this surface 78a is tubular or straight-walled.

In another embodiment, the piercing member 80a of the smaller enfitment 18a has a helical shape which culminates in a raised sharp tip 94a. The tip initially punctures a small hole in the bag. As the enfitment 18a is rotated, the flexible bag is forced between the downwardly spiraling edge of the piercing member 80a and the flange 76a.

To detach the flexible bag from the enfitment 18a, the bag is constrained between the flange 76a and the piercing member 80a and the enfitment 18a is rotated clockwise. With further rotation of the enfitment 18a, the flexible bag is completely disengaged from the enfitment.

The end piece 72a can also include a drive gear 74a formed about its peripheral edge and below the flange 76a. The drive gear 74a desirably cooperates with a worm gear of a drive mechanism (not shown), similar to that described above. In this manner, the rotational orientation of the enfitment 18a can be automatically controlled.

In order to dispense a controlled amount of material from the flexible bag 22, the piston 14 is compressed against the bag 22 in through a series of discrete dispensation steps. Compression of the bag 22 by the piston 14 squeezes an amount of material from the bag. It is important to note that, because the bag can have an uneven shape, if the distance of piston travel is constant, the amount of material being dispensed from the bag 22 can vary, depending on the amount of material left in the bag. That is, as the system is continuously used with an individual flexible bag, the weight or volume of flexible material dispensed with an incremental piston displacement will initially increase in volume for the first few dispenses and then decrease as the bag nears empty. In addition, because the bag 22 may not precisely match the shape of the hopper 10, at least initially, the volume of the first several dispensations can vary if the piston 14 is moved incrementally.

Figure 19:
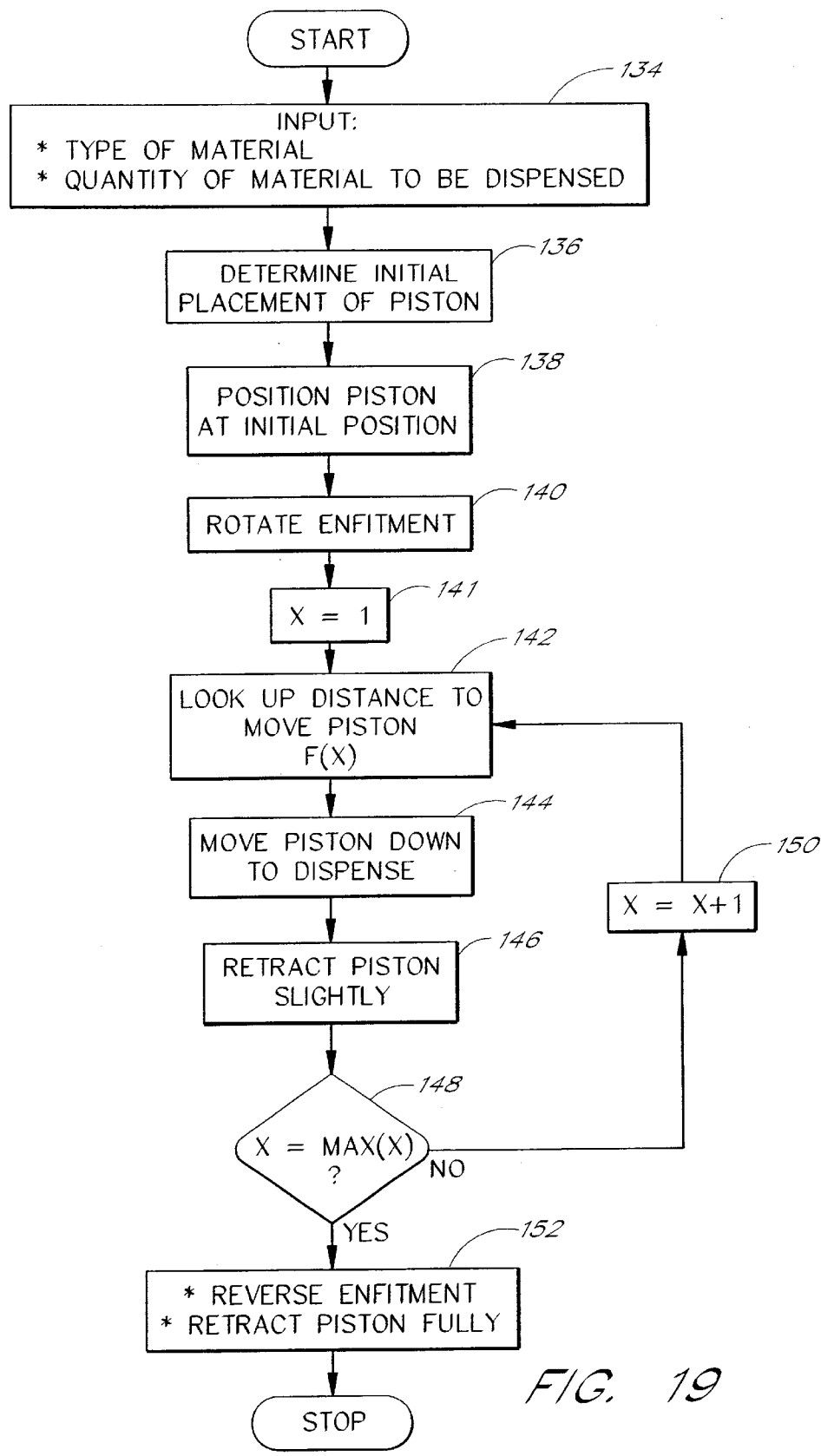
FIG. 19 is a flow chart illustrating the software control of the piston and enfitment.

The present system includes calibration software to determine the amount of piston displacement necessary to dispense consistent amounts of material regardless of the amount of product remaining in the bag 22. FIG. 19 illustrates the general steps of calibrating the operation of the piston 14. Since the amount of material dispensed will depend on the type of material, including the viscosity and density of the material, the user must first input the type of material to be dispensed (as shown in input box 134). In addition, the user must also input the quantity of material to be dispensed (also shown in input box 134). In some applications, the user can also input the desired volumetric size of each dispensation to account for differing applications. In such a case, the control computer 34 uses this information and computes the number of dispensation steps in the sequence which is required to dispense the entire quantity in equal-volume dispensations.

In some applications, however, it is desirable to vary the amount of material dispensed. For example, in the food industry a certain quantity of flexible material may be used for making one type of product, while a larger portion of material may be used for another product. The system 10 can be programmed for dispensation of variable amounts of material depending on the type of product or desired quantity of material.

As illustrated in operation block 136, the software determines the initial placement of the piston 14. In some applications, the initial position of the piston will differ from the normal initial position of the piston. For instance, if the bag 22 is only partially filled (or has already been partially depleted), or where the material is placed directly into the hopper 12 without being contained within a bag 22, the initial placement position of the piston 14 will need to be determined, for instance, by sensing the top of the bag containing material or the top of the material. The system can determine this initial position by using springs or a strain gauge device to determine when the resistance occurs to indicate that the top of the material has been reached. In another embodiment, the top of the material may be sensed through a constant torque motor by sensing the current draw. By comparing the sensed initial position to the normal initial position of the piston 14, the number of dispensation steps remaining can be determined.

After the initial placement position of the piston 14 is determined, the piston 14 is initially placed directly above the bag 22 with a slight downward pressure on the bag 22 (as represented in operation block 138). The system software controls this initial placement of the piston 14, as mentioned above.

With the bag 22 compressed against the bottom surface of the hopper 12 and the protruding enfitment 18, the enfitment 18 is rotated in a counterclockwise direction to puncture and stretch the bag 22 around the enfitment 18 (as represented in operation block 140). As discussed above, the enfitment 18 forms a seal with the bag 22 so that the food product may be dispensed through the hollow tube 70 of the enfitment 18.

The calibration software provides a means of directing the displacement of the piston 14 to achieve a desired weight or volume dispensed regardless of the dispense number or the desired dispensed volume. In most cases, the packaging of the product in the flexible bag is held constant, i.e. weight and size of the bag and material is the same for each product or material. If, however, the packaging of the product varies, such as by weight or size, the software can adjust the initial placement of the piston 14 as discussed above, and can also determine the piston displacement for each dispensation of such quantity.

To achieve the necessary correction or calibration to obtain the desired dispense weight or volume, a data table is formulated based on one or more of the following: the type of material to be dispensed, the viscosity and density of the flowable material, the quantity of material to be dispensed (i.e., the initial volume of the bag), the total number of dispensation steps to be performed, the volume of material to be dispensed during each dispensation step, and the number of dispensations already achieved from the bag. It is also necessary to determine when the curve in the top wall of the bag 22 becomes flat and if air in the bag 22 causes errors in the dispensed weight or volume. The weights/volume versus dispense number for each test run is then averaged to obtain the best overall numbers. Using this data, a piston displacement table is made for the initial dispenses, for consistent variations along the middle of the curve and for the last dispenses of material from the bag. The control computer 34 uses the tables, which are stored in memory within the computer 34, to determine the piston displacement for the desired volume/weight at the current dispense number.

Figure 20:
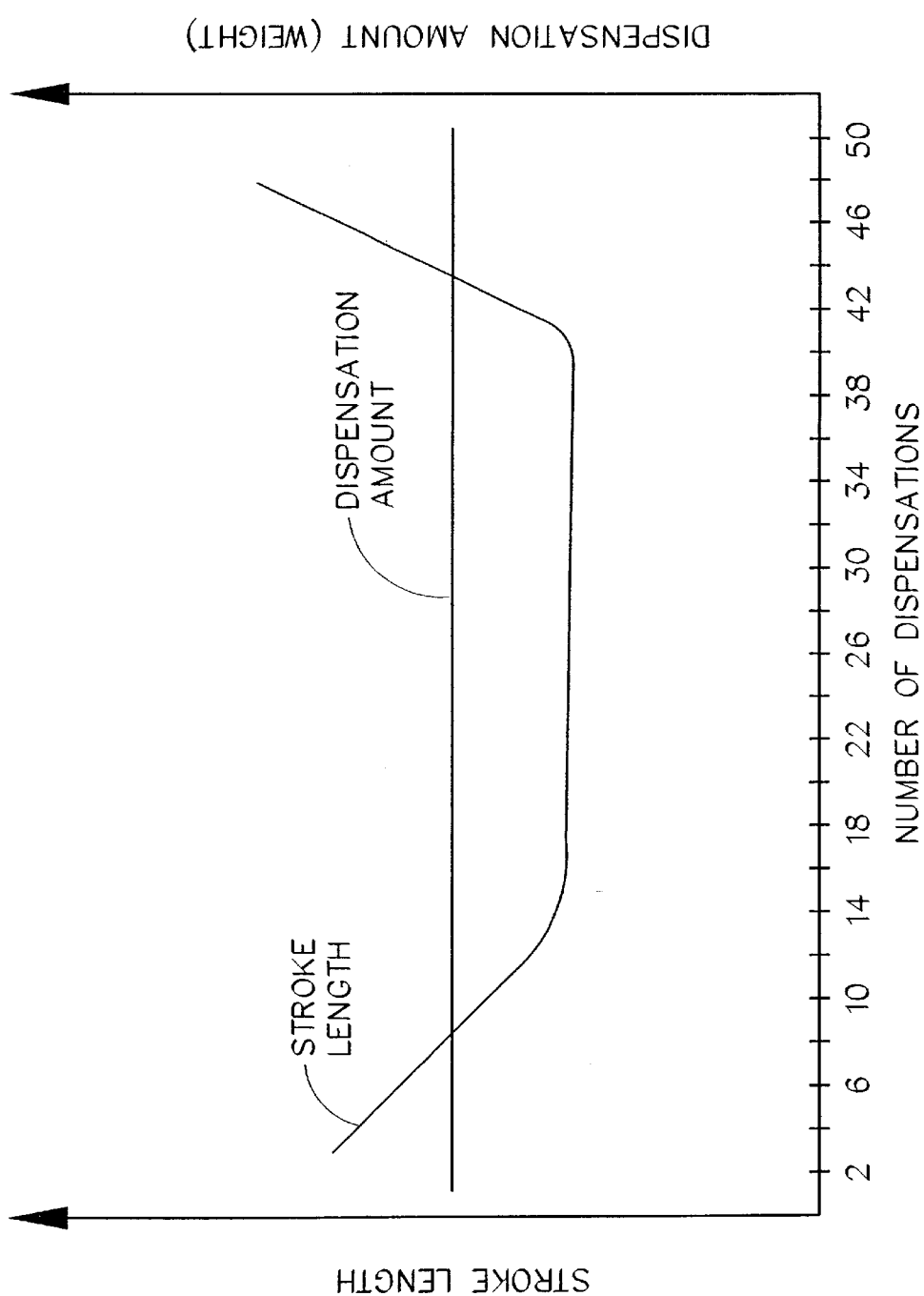
FIG. 20 is a graph of stroke length versus dispensation over a number of dispensations, and of the weight of material dispensed over the dispensations, illustrating a non-uniformity of stroke length between dispensations that in some applications is desired in order to dispense uniform quantities or weights of material.

From empirical data, it has been determined that stroke length of the piston during the first several dispensation steps and during the last few dispensation steps should be greater than the stroke length associated with dispensation steps in the middle of the sequence (e.g., the median dispensation step). As seen in the graph of FIG. 20, the required stroke length gradually decreases from the initial dispensation step to a generally constant stroke length associated with the middle steps. The last few dispensation steps, however, as the bag 22 empties require a longer stroke length to dispense the same volume of flowable material. The piston may have to move during the last dispensation step by a stroke length greater than the stroke length associated with the first dispensation step, as illustrated in FIG. 20; however, in some cases, the reverse may be true.

With returned reference to FIG. 19, for the first dispensation from the bag 22, the variable x, which represents the number of displacements, is one (as represented in operation block 141). Using this information and the information already input by the user, the computer 34 accesses the data table to determine the piston displacement to dispense the desired quantity of material (as represented by operation block 142). The computer 34 then directs the piston 14 to move the desired distance to compress the bag 22 against the bottom and side walls of the hopper 12 (as represented by operational block 144). The compression of the bag 22 forces an amount of material from the bag which is dispensed through the exit nozzle 20.

The first position controlled motor 36 that moves the piston 14 is also reversible, and is used to cause the piston 14 to back-up at the end of each dispensation step (as represented by operational block 146). In this manner, the pressure on the diaphragm 66 is reduced so that the exit slits on the diaphragm 66 close more completely. Therefore, nozzle dripping between dispensations is reduced or eliminated. For each size bag and desired dispensation amount, there is a preset number of dispensation steps until the bag 22 is emptied. The number of dispensation steps is predetermined based upon the initial volume of material within the bag and the quantity of material dispensed at each dispensation step as well as the viscosity and density of the material. If the maximum number of dispensations is reached (x=max(x)), as represented in decision block 148, the second position controlled motor 130 rotates the enfitment 18 in a direction that unwinds the enfitment 18 from the bag 22 to remove the bag 22 from the enfitment 18 and to unseal the bag 22. In addition, the piston 14 is fully retracted from the hopper so that no pressure is placed on the bag 22 (as represented by operation block 152).

If, however, the maximum number of dispensations has not been reached, i.e. there is dispensable material remaining in the bag, the dispensation counter is increased by one (as represented in operation block 150) and the data table is again accessed to determine the pre-established piston travel distance for that specific dispensation step. This cycle is repeated until all or at least substantially all of the material is dispensed from the bag.

The control parameters for the system, including the calibration software, can be stored in memory and maintained at remote location from the system. Instructions for controlling the system 10 can be communicated to the system via modem or other method communication. In this manner, the software can be updated and maintained at a central location and communicated to the system. In addition, operation of the system can also be controlled from a remote location. For instance, a user can actuate dispensation of multiple types of material each from separate system that is centrally controlled at a remote location.

In another embodiment, the system can be made to maintain constant pressure on the bag 22. This can be done by either replacing the incremental motor 36 with a constant torque motor, or by modifying the mechanism shown in FIG. 1 by adding springs or a strain gauge device and linear bearings. The motor 36 again drives lead screw 38 by way of the pulleys 40 coupled via a belt 42. The lead screw 38 again drives the assembly consisting of the nut 44, the nut plate 46, the transfer shafts 48, 50, and the piston 14. However, when piston 14 reaches the flexible bag 22, the springs are compressed. The distance the springs compress is determined by either a linear sensor or switch, which is actuated by a bracket attached to a transfer shaft and piston.

Although this invention has been described in terms of certain preferred embodiments, other embodiments apparent to those of ordinary skill in the art are also within the scope of this invention. For instance, certain features of the present invention can be used in an apparatus for dispensing various types of flowable material, including, but not limited to caulking, adhesives, grease, etc. A housing or caulking gun can be configured to receive a flexible-walled container (e.g., a cartridge) which holds the material to be dispensed. An enfitment such as the one described above, or one known to those of ordinary skill in the art, can be unitary with or connected to the refillable or replaceable cartridge. In other embodiments, the enfitment is connected to or unitary with the caulking gun. After placement of the cartridge within the housing, a piston within the housing is moved along a stroke axis to compress the flexible-walled cartridge so that a predetermined amount of flowable material is dispensed.

The present invention is not limited by the description of the preferred embodiments. Similarly, a dispensation system or apparatus need not include all of the features described above. Thus, the scope of the invention is intended to be defined only by the appended claims.

What is claimed is:

1. A system for dispensing controlled amounts of flowable material stored in a flexible-walled container, the system comprising a housing configured to hold the flexible-walled container, a piston positionable within the housing to apply pressure to the flexible-walled container so as to compress the flexible-walled container, a drive mechanism coupled to the piston to move the piston along a stroke axis, and a position controlled motor coupled to the drive mechanism to move the piston between a plurality of discrete positions along the stroke axis.

2. The system of claim 1 additionally comprising a controller for determining the amount of piston displacement required to dispense a predetermined quantity of the flowable material, the controller being connected to the motor for control thereof.

3. The system of claim 2, wherein the controller provides for reversal of the displacement direction of the piston at the end of each dispensation step to relieve pressure of the flowable material in the flexible-walled container.

4. The system of claim 3, wherein the controller is configured to reposition the piston to the position of the piston prior to reversal of the displacement direction of the piston at the end of each dispensation step.

5. The system of claim 1, wherein the drive mechanism comprises a rack and pinion device.

6. The system of claim 1, wherein the drive mechanism includes a shaft and a nut.

7. The system of claim 6, wherein the piston is coupled to the shaft such that axial movement of the shaft moves the piston along the stroke axis.

8. The system of claim 1, wherein the drive mechanism comprises a jack screw device.

9. The system of claim 1 additionally comprising an enfitment connected to the housing, the enfitment adapted to cooperate with the flexible-walled container to provide an opening in the flexible-walled container for dispensing flowable material from the flexible-walled container.

10. The system of claim 9, wherein the piston applies pressure on a side of the flexible-walled container generally opposite a side of the flexible-walled container which interacts with the enfitment.

11. The system of claim 1, wherein the flexible-walled container includes an enfitment.

12. The system of claim 11, wherein the piston applies pressure on a side of the flexible-walled container generally opposite a side of the flexible-walled container which interacts with the enfitment.

13. A system for dispensing controlled amounts of flowable material stored in a flexible-walled container, the system comprising a housing configured to hold the flexible-walled container, a piston, an actuator connected to the piston to drive the piston along a stroke axis, said actuator including a screw, a ball nut engaged with the screw and coupled to the piston such that the ball nut and piston move along the stroke axis relative to the screw, and a motor drivingly coupled to the screw so as to move the piston along the stroke axis, and a controller connected to the actuator and configured to control piston movement along the stroke axis so as dispense a controlled amount of flowable material from the flexible-walled container.

14. The system of claim 13, wherein the flexible-walled container includes an enfitment.

15. The system of claim 13, wherein the piston has a complementary cross-sectional shape, as taken generally normal to the stroke axis of the system, to that of the flexible-walled container.

16. The system of claim 13 additionally comprising means for determining piston displacement required to dispense a predetermined amount of flowable material from the flexible walled container.

17. The system of claim 13, wherein the motor moves the piston between a plurality of positions which correspond to distinct dispensation steps within a controlled travel range of the piston.

18. The system of claim 12, wherein the plurality of positions along the stroke axis are not at uniform increments.

19. The system of claim 13, wherein the motor is bi-directional to provide for reversal of the displacement direction of the piston at the end of each displacement step so that pressure of the flowable material in the flexible-walled container is relieved.

20. The system of claim 19, wherein the controller provides for moving the piston from a first position where pressure of the flowable material in the flexible-walled container is relieved to a second position where the piston was positioned at the end of a dispensation step.

* * * * *